US011389285B2

(12) United States Patent
Park et al.

(10) Patent No.: US 11,389,285 B2
(45) Date of Patent: Jul. 19, 2022

(54) THREE DIMENSIONAL TRACHEAL SUBSTITUTE REPLACING RESPIRATORY ORGANS AND METHOD OF PRODUCING THE SAME

(71) Applicants: POSTECH Research and Business Development Foundation, Pohang-si (KR); THE CATHOLIC UNIVERSITY OF KOREA INDUSTRY-ACADEMIC COOPERATION FOUNDATION, Seoul (KR); Gachon University of Industry-Academic cooperation Foundation, Seongnam-si (KR)

(72) Inventors: Jeong Hun Park, Pohang-si (KR); Dong-Woo Cho, Seoul (KR); Jung-Seob Lee, Yangsan-si (KR); Ju Young Park, Daegu (KR); Min Jun Ahn, Busan (KR); Inn Chul Nam, Seoul (KR); Sung Won Kim, Seoul (KR); Jae Yeon Lee, Pohang-si (KR); Jin Woo Lee, Incheon (KR); Sun Hwa Park, Seoul (KR); Byeong Gon Yun, Seoul (KR)

(73) Assignees: POSTECH RESEARCH AND BUSINESS DEVELOPMENT FOUNDATION, Pohang-si (KR); THE CATHOLIC UNIVERSITY OF KOREA INDUSTRY—ACADEMIC COOPERATION FOUNDATION, Seoul (KR); GACHON UNIVERSITY OF INDUSTRY—ACADEMIC COOPERATION FOUNDATION, Seongnam-si (KR)

( * ) Notice: Subject to any disclaimer, the term of this patent is extended or adjusted under 35 U.S.C. 154(b) by 237 days.

(21) Appl. No.: 16/616,593

(22) PCT Filed: Jun. 2, 2017

(86) PCT No.: PCT/KR2017/005800
§ 371 (c)(1),
(2) Date: Nov. 25, 2019

(87) PCT Pub. No.: WO2018/221764
PCT Pub. Date: Dec. 6, 2018

(65) Prior Publication Data
US 2020/0163747 A1 May 28, 2020

(30) Foreign Application Priority Data
May 29, 2017 (KR) .................. 10-2017-0066302

(51) Int. Cl.
*B33Y 10/00* (2015.01)
*A61F 2/00* (2006.01)
(Continued)

(52) U.S. Cl.
CPC .............. *A61F 2/04* (2013.01); *A61L 31/047* (2013.01); *A61L 31/146* (2013.01); *B33Y 10/00* (2014.12);
(Continued)

(58) Field of Classification Search
CPC ......... A61F 2240/001; A61F 2240/002; A61L 2420/02; B33Y 10/00
See application file for complete search history.

(56) References Cited

U.S. PATENT DOCUMENTS

2016/0051385 A1 2/2016 Hollister et al.

FOREIGN PATENT DOCUMENTS

| KR | 10-1067827 | 9/2011 |
| WO | 2017-032837 | 3/2017 |

OTHER PUBLICATIONS

Park et al. "A novel tissue-engineered trachea with a mechanical behavior similar to native trachea" Biomaterials. 62 pp. 106-115 (2015) (Year: 2015).*

(Continued)

*Primary Examiner* — Cachet I Proctor
(74) *Attorney, Agent, or Firm* — Lex IP Meister, PLLC

(57) ABSTRACT

The present invention relates to a bellows framework having a concave-convex structure on at least one of outer and inner sides using three-dimensional printing technology and a method of producing thereof, and an artificial tracheal replacement comprising an epithelium part formed on the inner side of the bellows framework and an annular cartilage part formed along the circumference of concave-convex grooves on the outer side and a method of producing thereof.

12 Claims, 16 Drawing Sheets
(14 of 16 Drawing Sheet(s) Filed in Color)

(51) Int. Cl.
| | | |
|---|---|---|
| *A61L 24/00* | (2006.01) | |
| *A61F 2/04* | (2013.01) | |
| *A61L 31/04* | (2006.01) | |
| *A61L 31/14* | (2006.01) | |
| *B33Y 80/00* | (2015.01) | |

(52) U.S. Cl.
CPC ....... *B33Y 80/00* (2014.12); *A61F 2002/0081* (2013.01); *A61F 2002/046* (2013.01); *A61F 2240/001* (2013.01); *A61F 2240/002* (2013.01); *A61L 2420/02* (2013.01); *A61L 2430/06* (2013.01)

(56) References Cited

OTHER PUBLICATIONS

Park et al. Development of a 3D bellows tracheal graft: mechanical behavior analysis fabrication and an in vivo feasibility study, bio fabrication. Apr. 2012 (Year: 2012).*
Park, J. H. et.al., "A Rational 3D Printing Strategy for Creation of Life-sized Tracheal Analogue", The Korean Association of Stem Cell & Tissue Regeneration, Dec. 4, 2016, p. 7.
HA,D.H. et al., "Development of bioink embedded esophageal stent for radiation esophagitis based on the 3D printing system" (abstract only), Proceedings of KSPE 2017 Conference, May 17, 2017, p. 404.
Jeong Hun Park et al., "A novel tissue-engineered trachea with a mechanical behavior similar to native trachea", vol. 6, pp. 106-115 (May 2015.).
Jeong Hun Park et al., "Development of a 3D bellows tracheal graft: mechanical behavior analysis, fabrication and an in vivo feasibility study". Biofabrication, vol. 4, No. 3, pp. 1-10(Aug. 2012.).
Chen-Huan Lin et al., "Evaluation of Type II Collagen Scaffolds Reinforced by Poly(epsilon-Caprolactone) as Tissue-Engineered Trachea", Tissue Engineering; Part C, 2008, V.14, No. 1, p. 69-77.

* cited by examiner

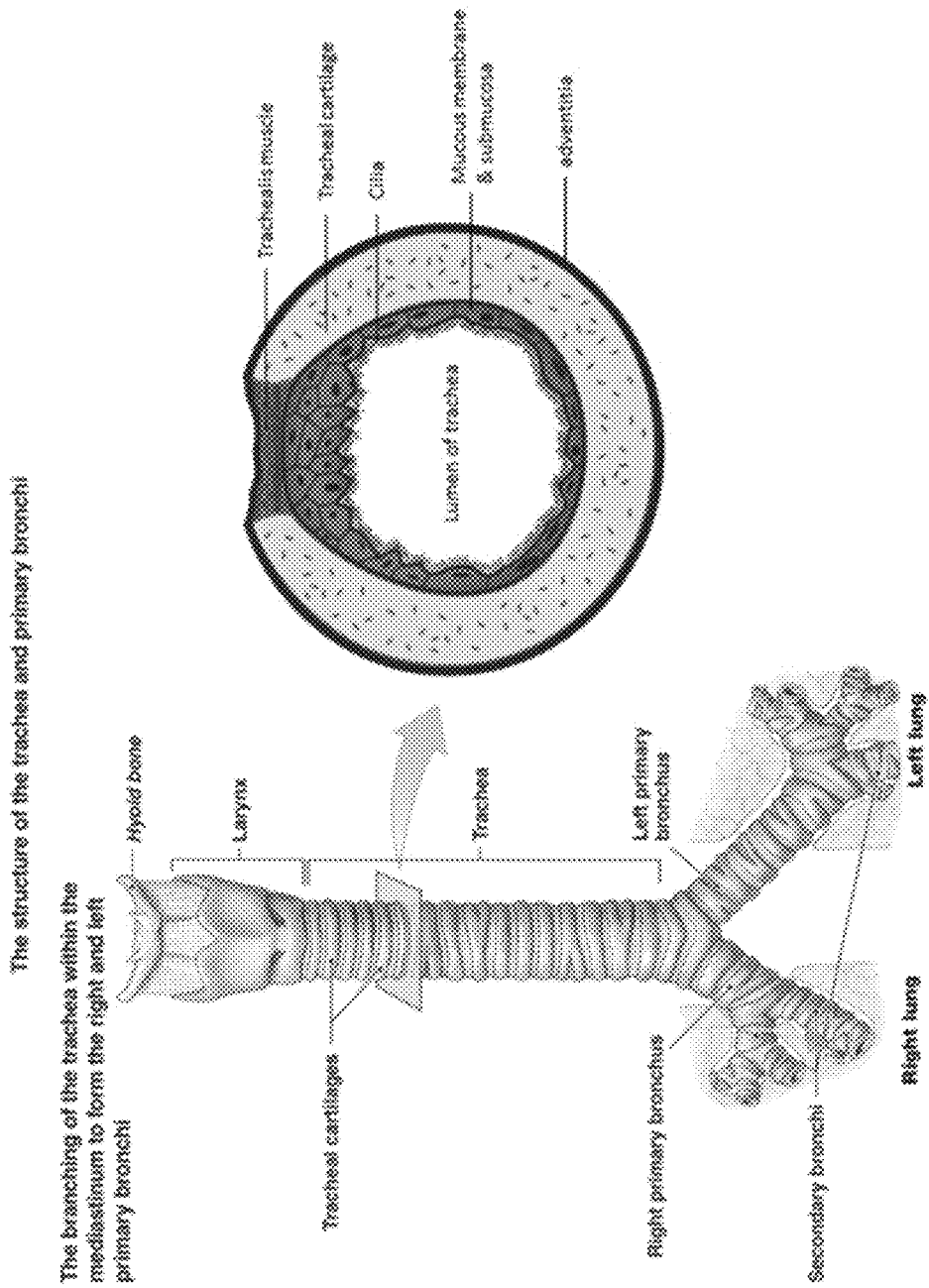

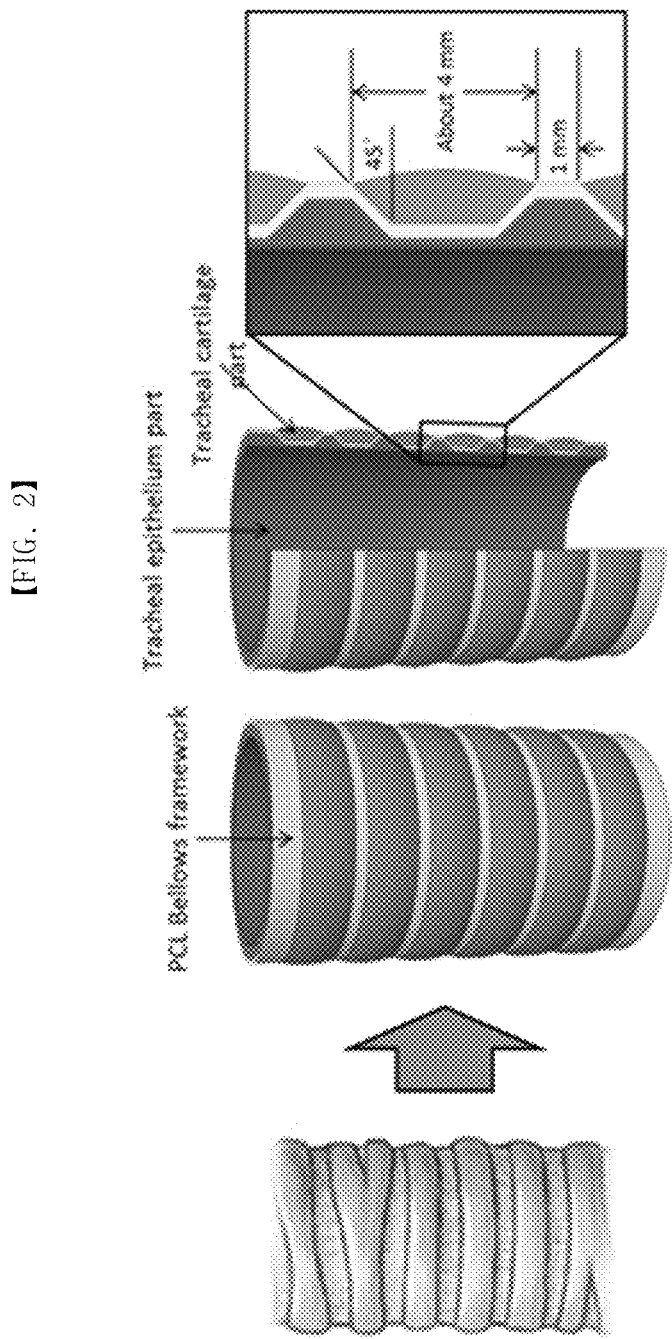
[FIG. 2]

[FIG. 3]
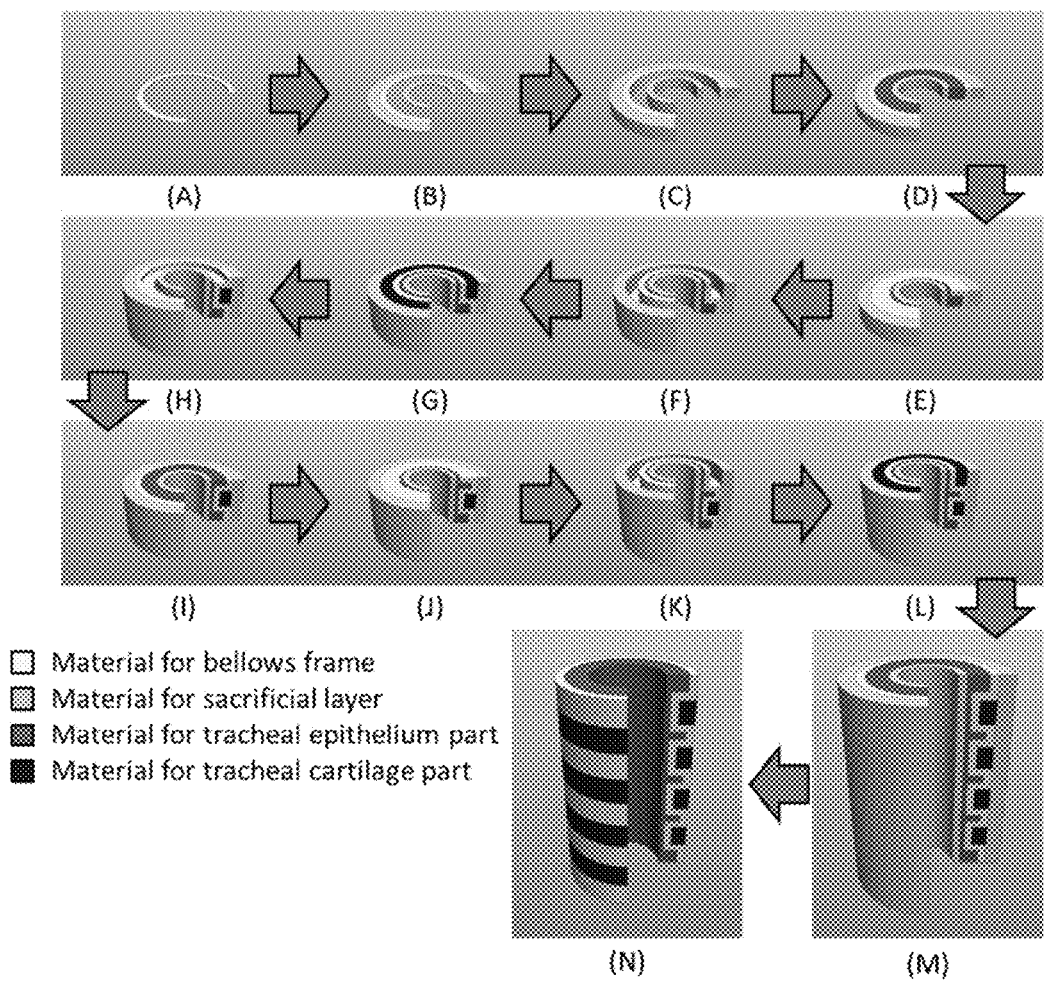

[FIG. 4]
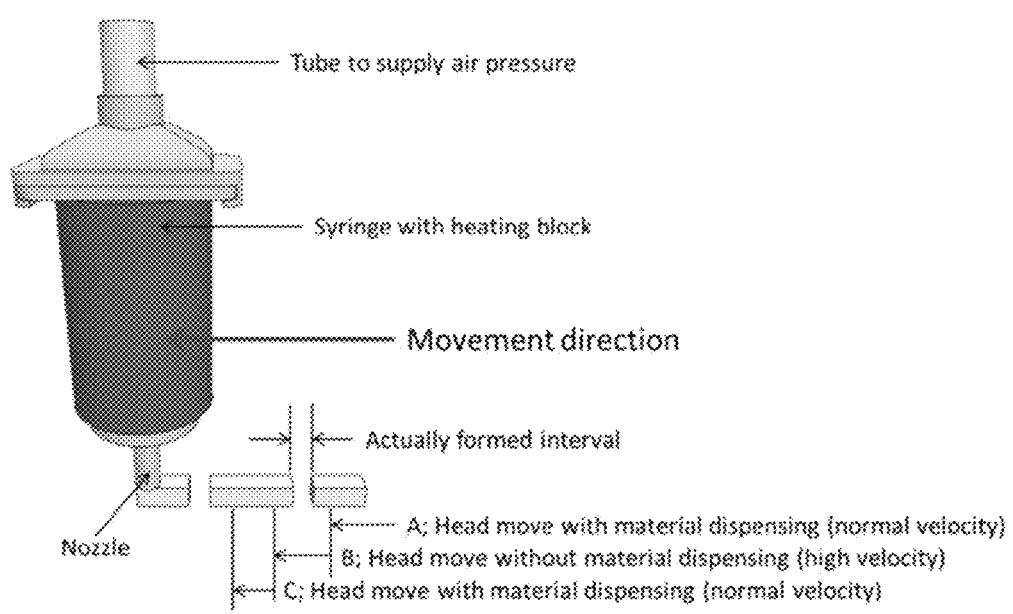

[FIG. 5]
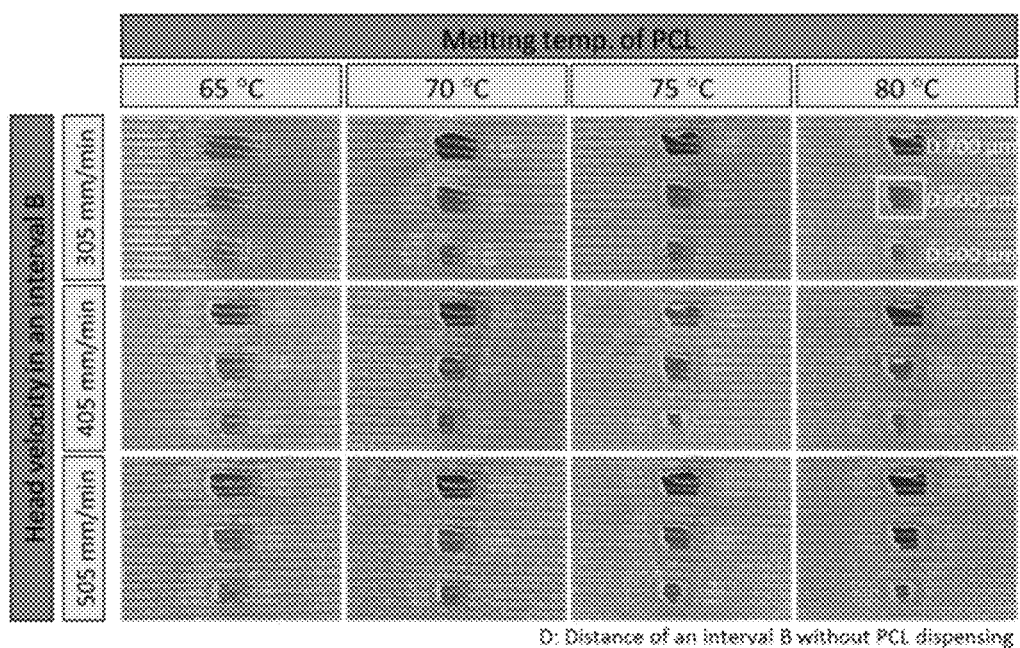

[FIG. 6]
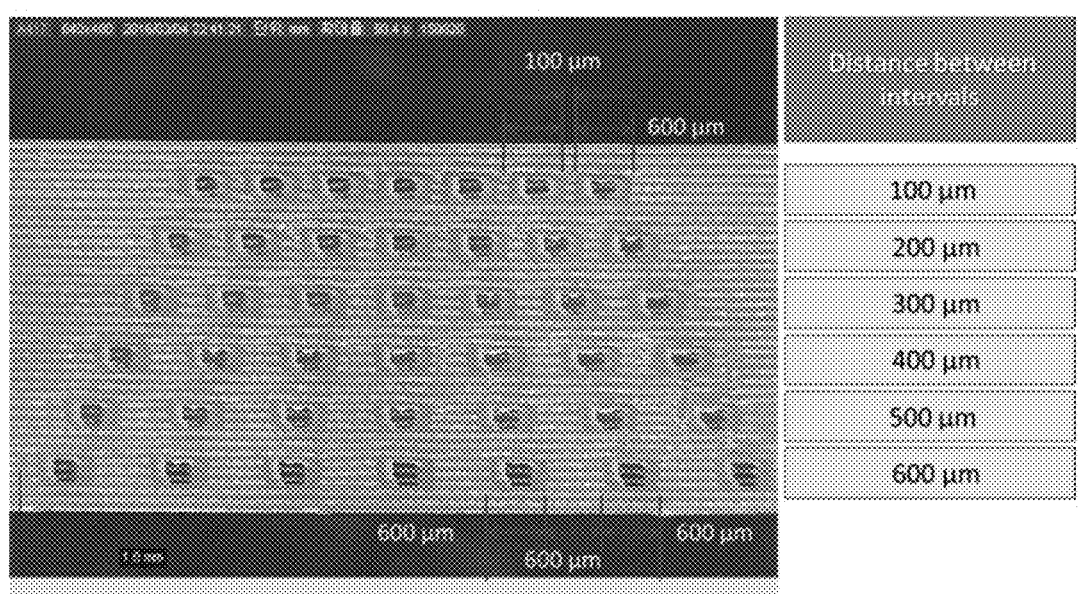

[FIG. 7]
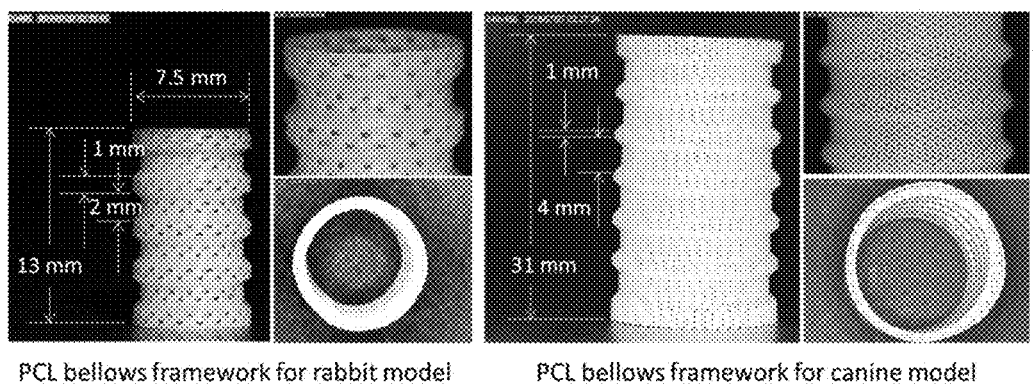
PCL bellows framework for rabbit model    PCL bellows framework for canine model

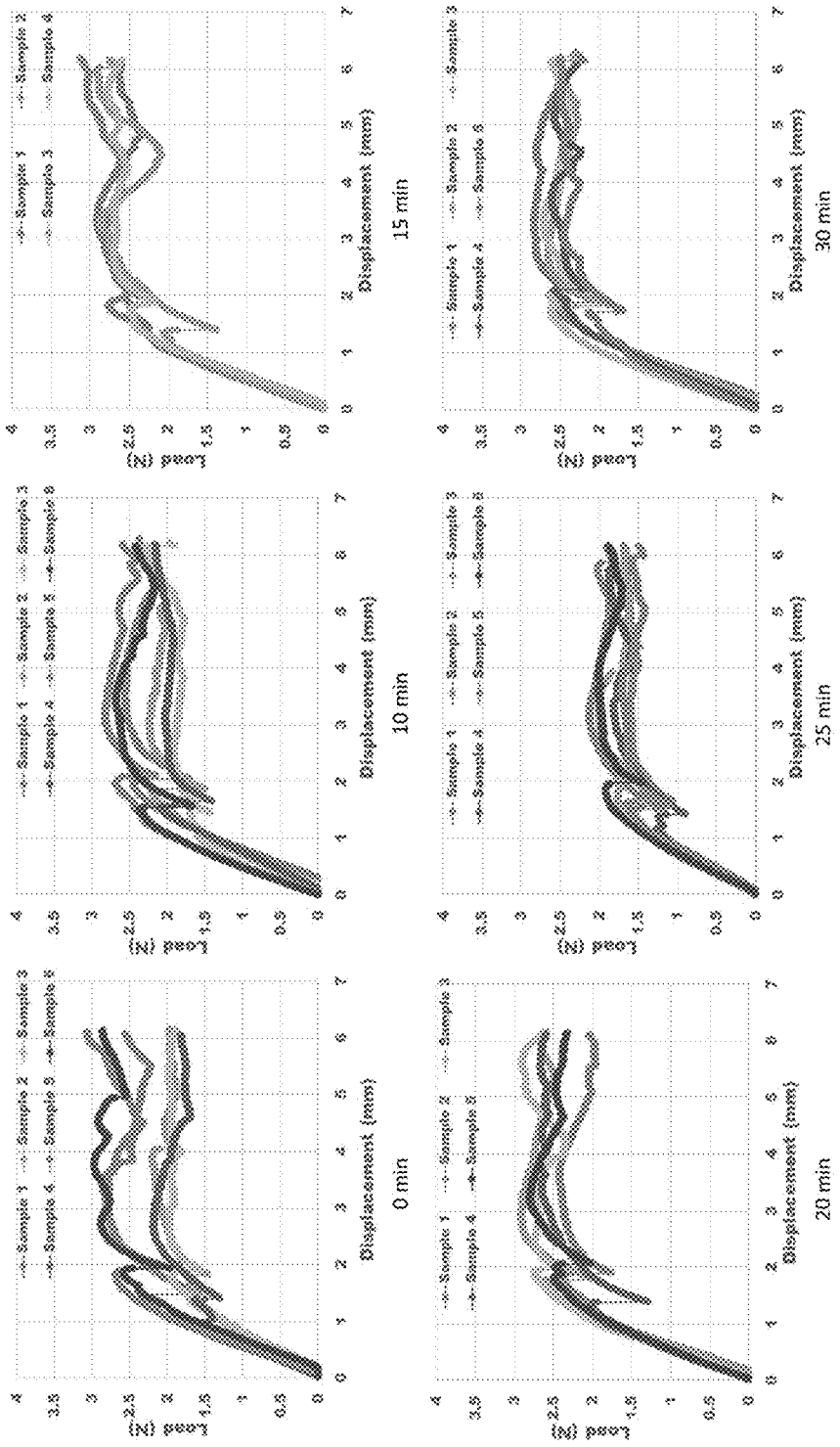
[FIG. 8]

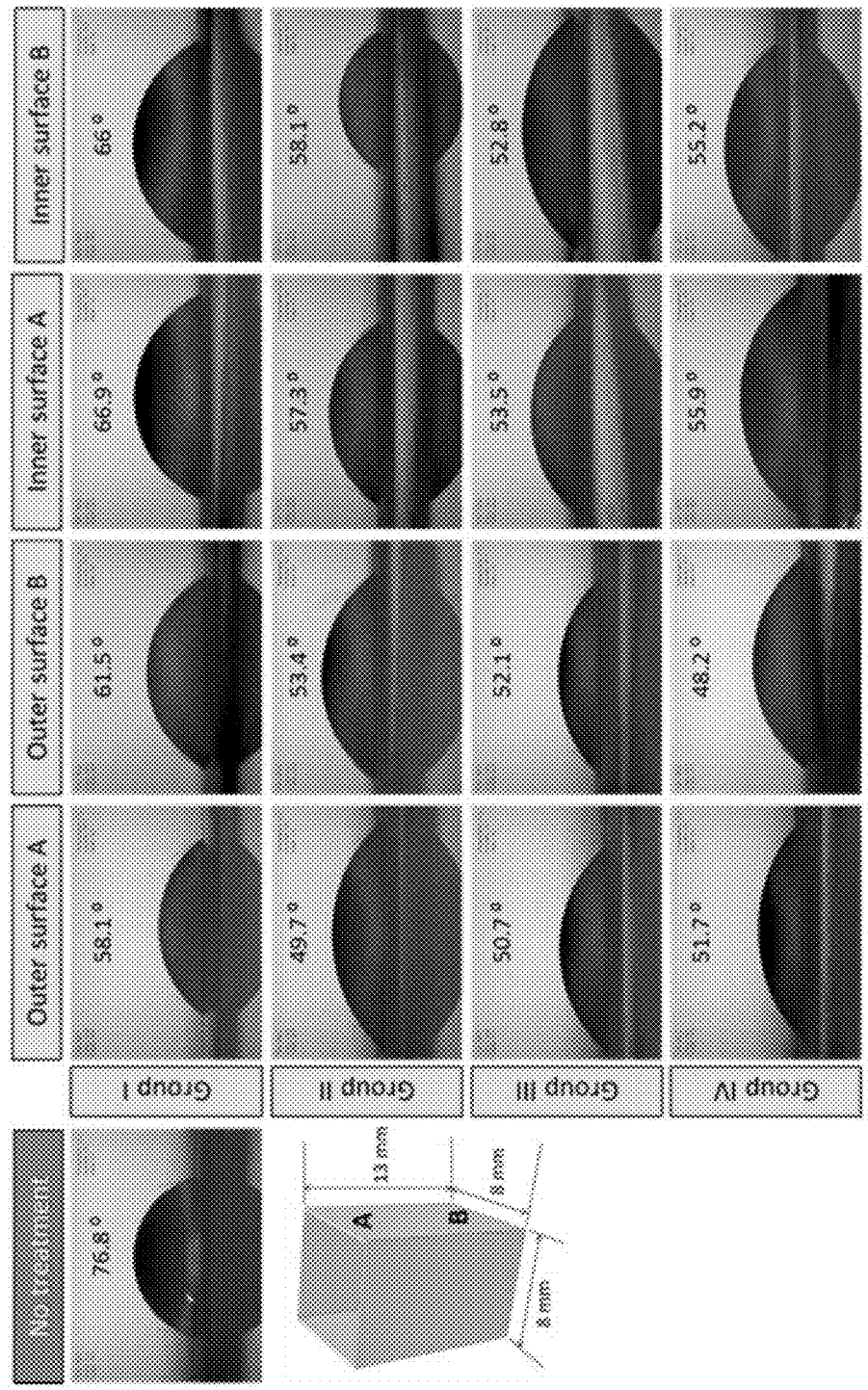
[FIG. 9]

[FIG. 10]
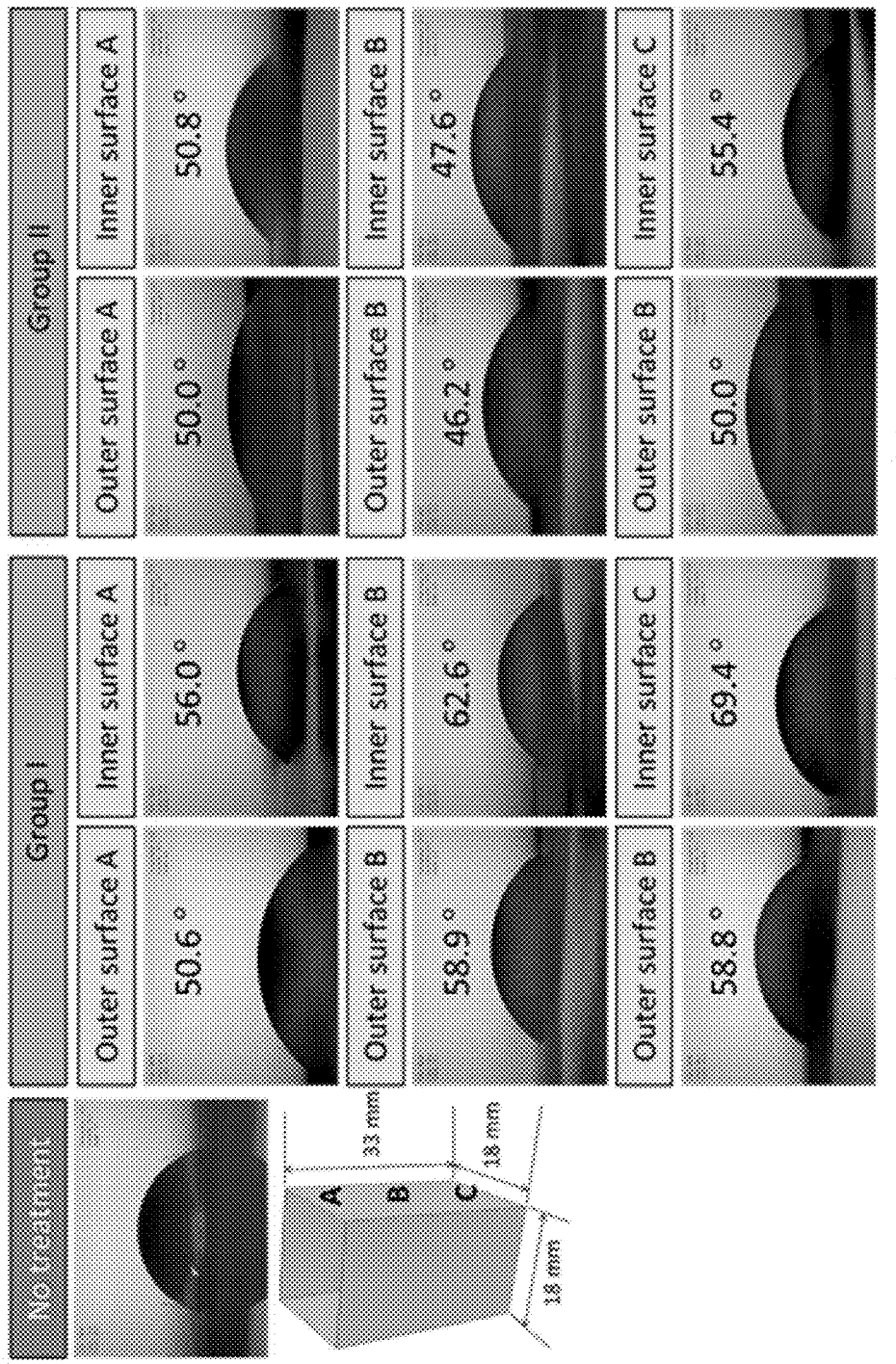

[FIG. 11]
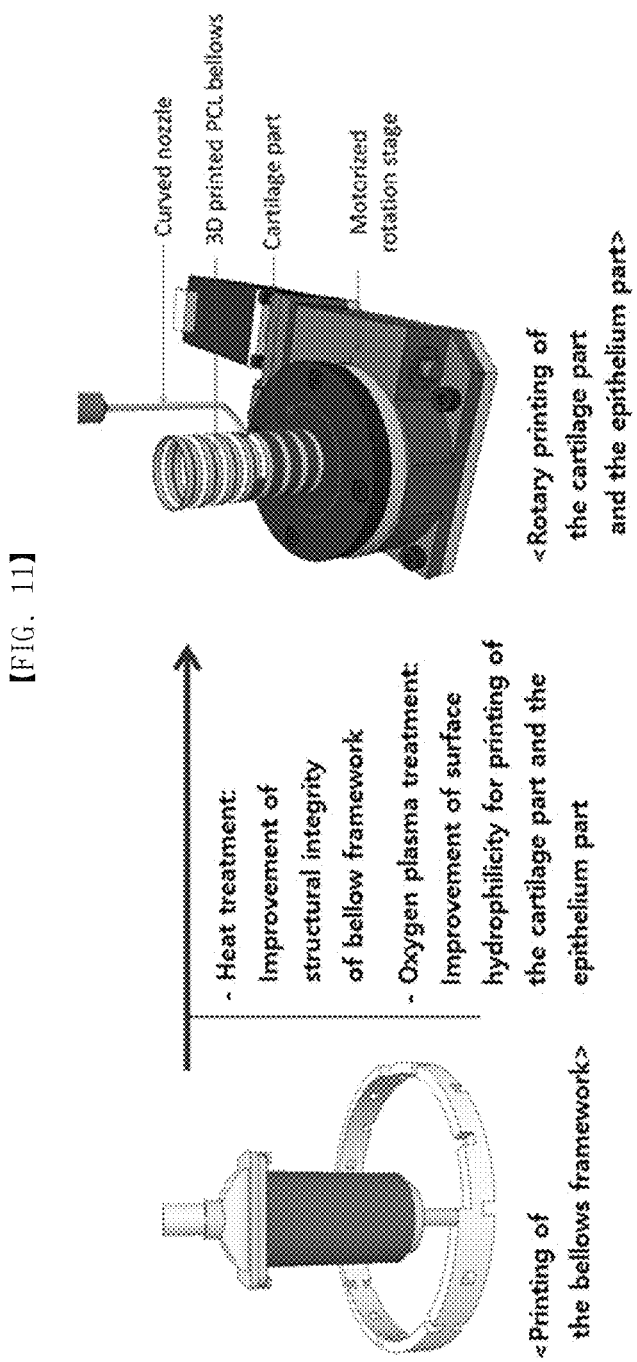

[FIG. 12]
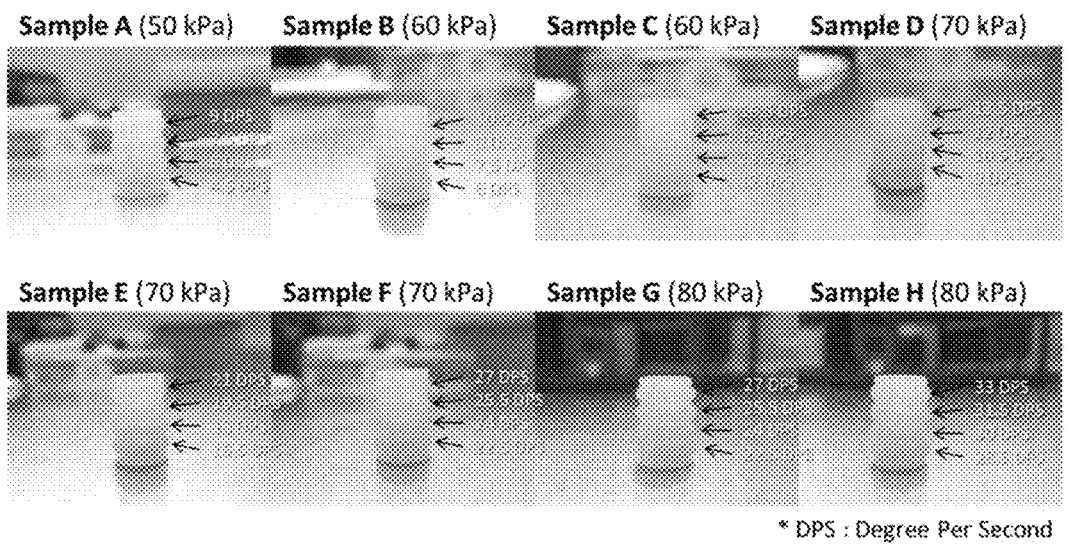
* DPS : Degree Per Second
[FIG. 13]
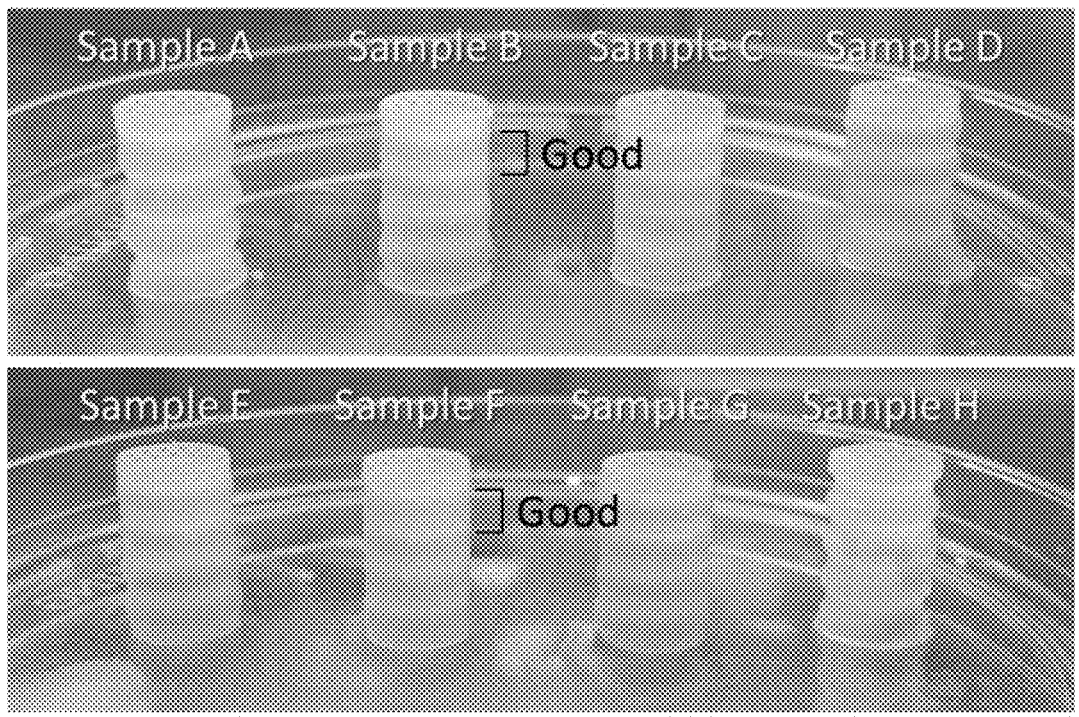

[FIG. 14]
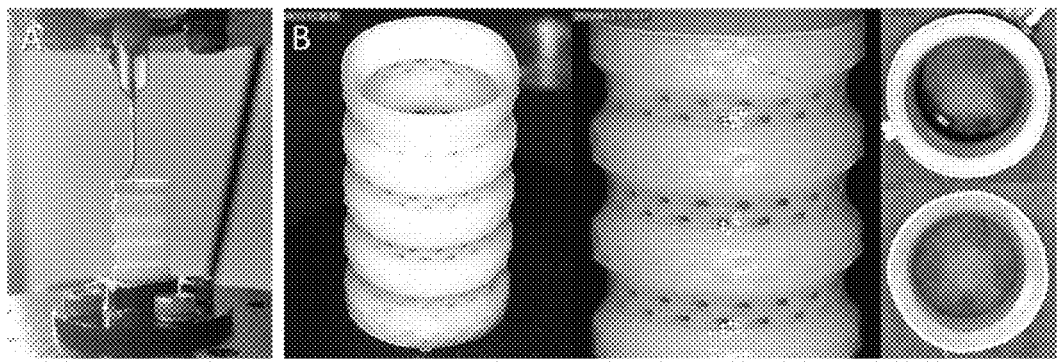
[FIG. 15]
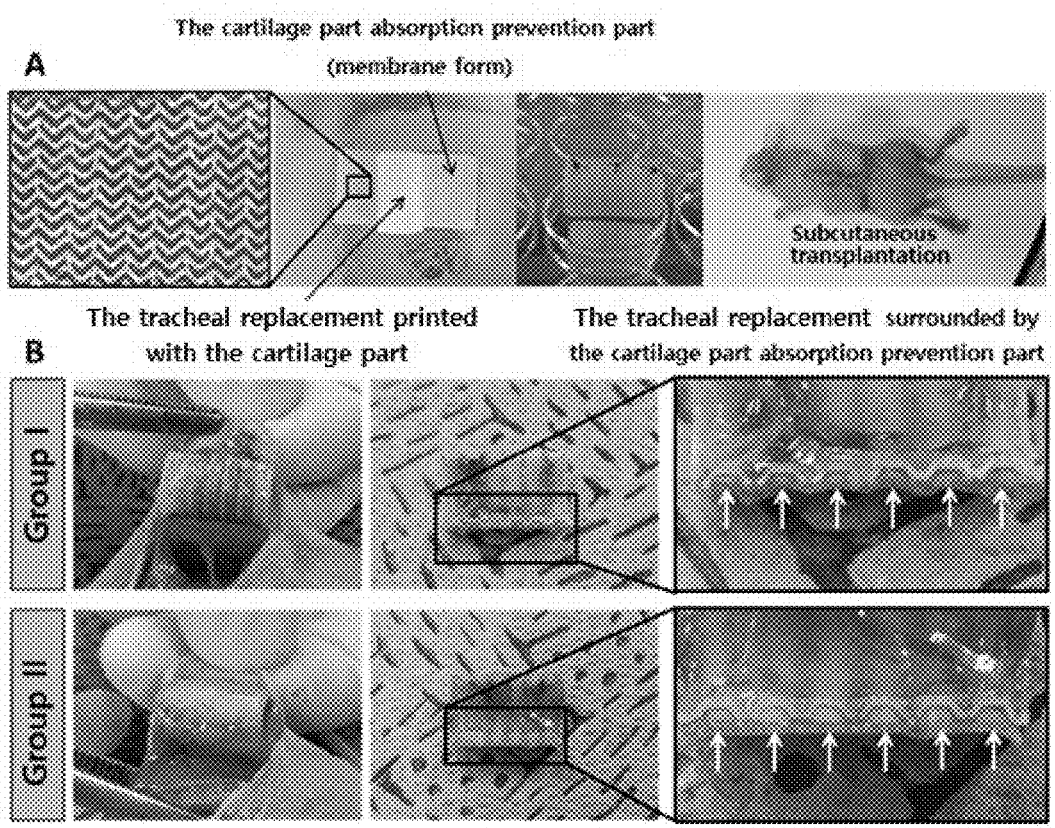

[FIG. 16]
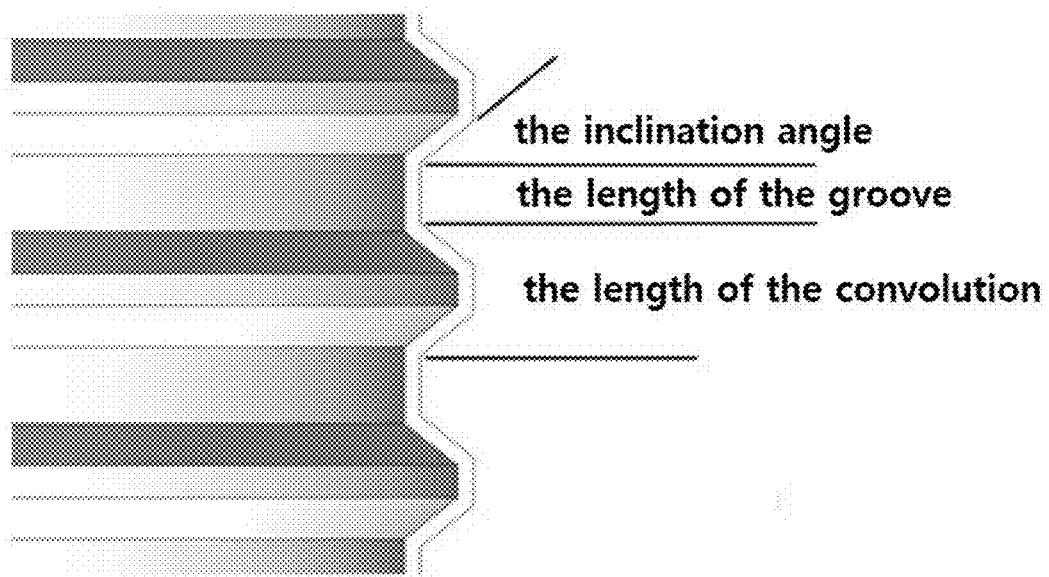

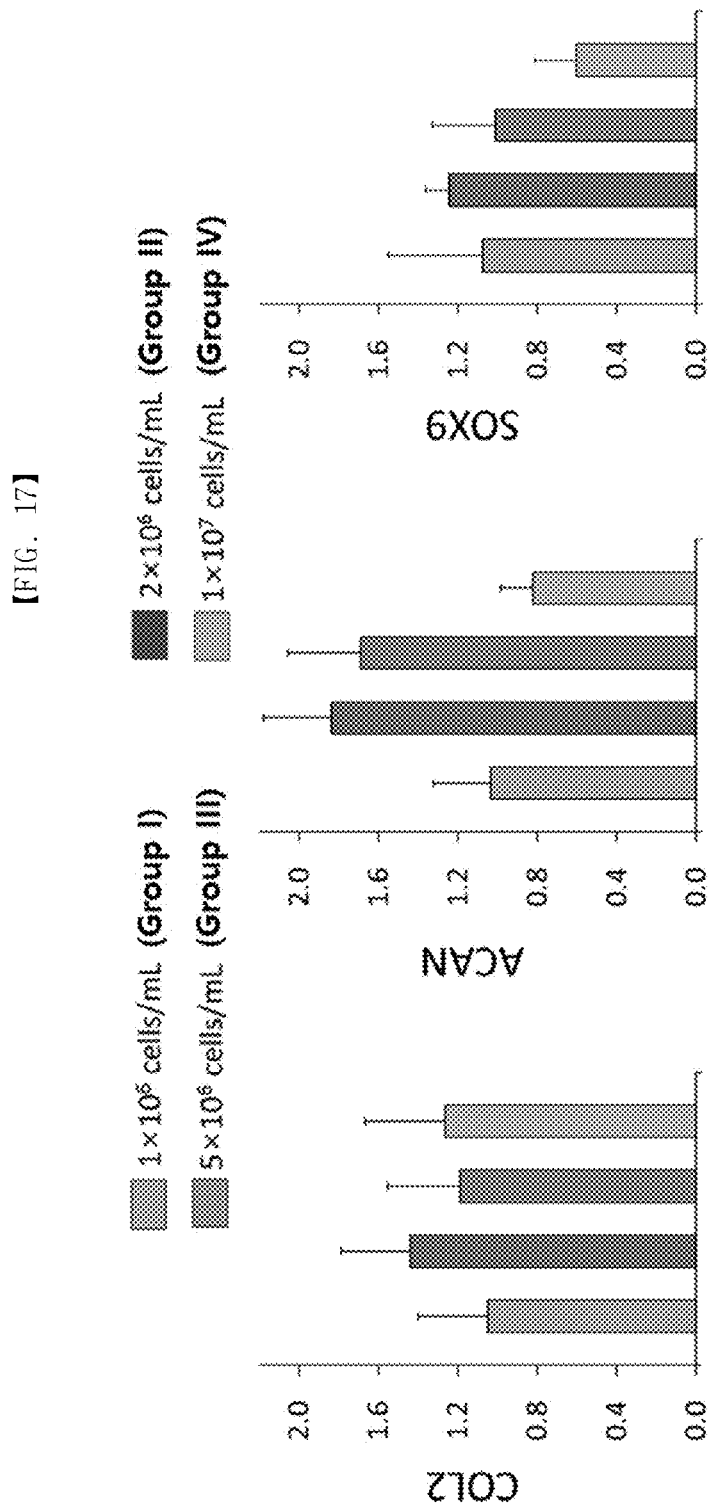
[FIG. 17]

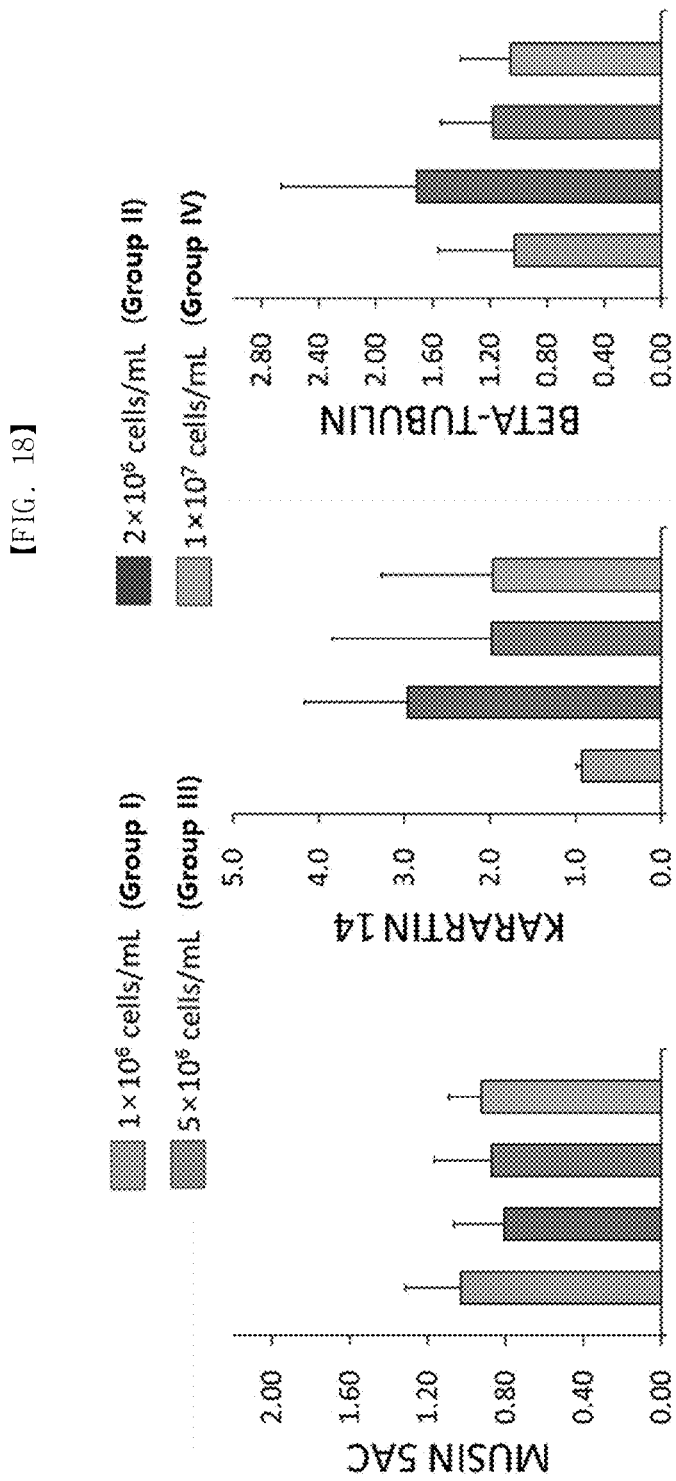
[FIG. 18]

THREE DIMENSIONAL TRACHEAL SUBSTITUTE REPLACING RESPIRATORY ORGANS AND METHOD OF PRODUCING THE SAME

TECHNICAL FIELD

The present invention relates to a tracheal replacement and a method of producing the same with three-dimensional printing technology.

BACKGROUND ART

According to an investigation by World Health Organization (WHO), bronchial diseases and lung cancer are the third among top ten causes of death in developed countries. In addition, as the survival rate of premature infants increases due to recent medical development, and the number of patients who need to be undergone long-term intensive care increases due to aging of the population, the incidence of tracheal defects due to long-term intratracheal intubation is increasing. In general adults, when the internal diameter of trachea narrows to 8 mm, respiratory distress occurs, and when it narrows to 6 mm, respiratory distress occurs so that daily life is difficult. When it narrows to 4 mm, it will be in the state just before the respiratory failure, which breathes with total mobilization of accessory respiratory muscles.

In case of tracheal defects, tracheal resection and end-to-end anastomosis, which removes a site of defects and seals the distal upper and lower ends, have been known as the most common standard operations. However, in case that the length of lesions is wide or congenital tracheal defects occur in infants, its application is difficult due to excessive tension of anastomosis. In general, in adults, resection within half of the total tracheal length is possible, and in infants and children, it is limited to about one third of the total length, since the tracheal tissue is weaker than adults.

Therefore, in order to treat a wide range of tracheal defects, a three-dimensional conduit type structure which can replace the excised defect site is needed. To this end, various histological methods using stem cells and hard supports have been attempted, but most of them are researches on respiratory mucosal epithelium and tracheal cartilage tissue regeneration in the local range. In reconstruction of extensive circular defects of trachea, respiratory mucosal epithelium hypoplasia has been reported on the internal surface of grafted supports, and hard supports which do not have the flexibility and patency of trachea cause granuloma overgrowth and tracheal occlusion due to excessive tension in anastomosis.

In this respect, for reconstruction of extensive circular defects of trachea, a new type of histological support considering mechanical•biological properties of trachea and simultaneous regeneration of respiratory mucosal epithelium and tracheal cartilage together is needed.

DISCLOSURE

Technical Problem

Accordingly, an embodiment of the present invention provides an artificial tracheal replacement, comprising a bellows framework which has concave-convex convolutions and grooves in a longitudinal direction on at least one side of outer and inner sides, an epithelium part formed on the inner side of the bellows framework, and an annular cartilage part formed along the circumference of the grooves.

In addition, the present invention provides a method of preparing a porous bellows framework having pores, repeatedly performing dispensing and non-dispensing of a melted thermoplastic polymer through a nozzle, and variably adjusting the movement speed of a dispensing head in each section, and adjusting the distance of the dispensing section and the distance of the non-dispensing section.

Furthermore, the present invention provides a preparation method of an artificial tracheal replacement, preparing a porous bellows framework which has concave-convex convolutions and grooves on at least one side of the outer and inner sides, preferably, on the inner side and outer side, by dispensing thermoplastic polymer melts using three-dimensional printing technology, and preparing an annular cartilage part on concave-convex grooves on the outer side of the porous bellows and preparing an epithelium part on the inner side using bio-ink.

Technical Solution

In the present invention, a new tracheal replacement having similar anatomical properties to the trachea in a human body has been developed based on a bellows structure. It is a new type of histological support which can have a mechanical behavior similar to the trachea of a human body having flexibility and patency by borrowing the bellows structure, and allows the simultaneous regeneration of the respiratory mucosal epithelium and tracheal cartilage of the trachea.

For preparation of this bellows framework, a new printing method capable of preparing a porous hollow wall type of structure using dispensing method-based three-dimensional printing technology has been developed. In addition, by separating printing of the bellows framework and the printing of the cartilage part and epithelium part in which cells can be comprised, the mechanical and material physical properties of the tracheal replacement are enhanced, and an optimized printing process capable of securing the survival and function of cells has been developed. In addition to that, to minimize the change of mechanical physical properties of the tracheal replacement and prevent internal absorption of the cartilage part in which cells can be comprised, an absorption prevention part of cartilage part which is combined to the outside of the tracheal replacement has been developed.

The present invention can copy the flexibility and patency which are mechanical properties of the trachea in a human body as they are based on the bellows framework. Accordingly, it is expected that side-effects after surgery due to the difference of mechanical physical properties between the trachea in the human body after grafted and the grafted analogue can be minimized, and the stability of patients to which the tracheal replacement is grafted can be maintained effectively. In addition, in that the tracheal replacement can achieve complete reconstruction of the trachea in a human body by considering simultaneous regeneration of the respiratory mucosal epithelium and tracheal cartilage, it may be a new customized medical device which can overcome limitations of conventional supports used in trachea reconstruction and can fundamentally treat intractable tracheal defects.

Moreover, the method of preparing a three-dimensional tracheal replacement in the present invention is a new type of preparation process based on three-dimensional printing in which the printing process of the bellows framework and the printing process of the cartilage part and the epithelium part are separated. Different from the conventional printing method in which cells are comprised in the total printing process, the time that cells are used in the printing process is shortened to a minimum, and thereby the survival and function of cells used in printing can be effectively secured, and this means that the performance of the three-dimensional tracheal replacement can be maximized. In addition, by adding a heating treatment process between the printing process of the bellows framework and the printing process of the cartilage part and epithelium part, limitations of the dispensing-based printing technology having not good binding capacity between layers are overcome. In addition to that, addition of the oxygen plasma treatment process makes preparation of a harder tracheal replacement possible by enhancing physical properties (surface hydrophilicity) used in preparation of the bellows framework. The heating treatment and oxygen plasma treatment processes may be added due to separation of the printing process of the bellows framework and the rotary printing process in which cells can be comprised, and by the development of such a separated printing method, preparation of a tracheal replacement copying mechanical•biological properties of the trachea in a human body as they are is possible.

Furthermore, the porous bellows framework in the present invention can be utilized as a standardized model in preparation of a structure for reconstruction of all conduit type of organs in a human body, as well as the trachea. In addition, the preparation method of the porous bellows framework and the rotary printing method can be applied for preparation of a new structure for reconstruction of various conduit types of organs.

The porous bellows framework according to one embodiment of the present invention has advantages that it may be prepared easily by the three-dimensional printing method using a biomaterial, and the shape and dimension of the bellows can be modified quite freely, and this can provide a tracheal replacement customized for a patient having a different size of airway, and there is no limitation even for the trachea damage range.

Hereinafter, the present invention will be described in more detail.

The trachea of a human body is a functional complex tubular frame structure, and consists of 4 layers in total of the respiratory mucosa consisting of mucous epithelium and lamina propria, submucosa, tracheal cartilage and adventitia from the inside (See FIG. 1).

The tracheal cartilage is a cartilage structure consisting of hyaline cartilage, and is a "C" type of incomplete cyclic structure surrounding about ⅔ of the circumference of the trachea, and it is facing forward of the body. The number of the tracheal cartilage is different from person to person, and commonly, 15~20 of them are distributed in the total length of the trachea, and the thickness in a longitudinal direction is approximately 4 mm. In addition, the radial thickness of the tracheal cartilage is known as approximately 1 to 1.5 mm. The annular ligament is present between the tracheal cartilage. The internal diameter of the trachea is approximately 19 mm, and the back and forth diameter of the tracheal cartilage is approximately 21 mm in men and approximately 17 mm in women, and the horizontal diameter is approximately 21.5 mm in men and approximately 17 mm in women.

One embodiment of the present invention provides a bellows frame having a surface concave-convex structure which has concave-convex convolutions and grooves in a longitudinal direction on at least one side of outer and inner sides.

Another embodiment of the present invention provides an artificial tracheal replacement, comprising a bellows frame having a surface concave-convex structure which has concave-convex convolutions and grooves in a longitudinal direction on at least one side of outer and inner sides, preferably, both the inner and outer sides, an epithelium part (tracheal epithelium part) formed on the inner side of the bellows framework, and an annular cartilage part (tracheal cartilage part) formed along the circumference of the outer side of the bellows framework.

The bellows framework according to the present invention is designed in consideration to the histological structure and properties of the trachea of a human body (See FIG. 2), and more specifically, the bellows framework having a surface concave-convex structure has the flexibility and patency, and is easy to maintain its shape, and the epithelium part is for regeneration of the respiratory mucosal epithelium tissue, and it has a structure covering the partial or whole internal surface of the bellows framework, and the cartilage part is a part for tracheal cartilage regeneration, and it is a structure annularly formed along the circumference of grooves between the outer convolutions of the bellows framework.

In additional one embodiment of the present invention, the artificial tracheal replacement according to the present invention may further comprise an absorption prevention part of cartilage part surrounding the outer side of the bellows framework equipped with the annular cartilage part, in addition to the bellows framework, epithelium part and cartilage part. The absorption prevention part of cartilage part is combined to the outside of the tracheal replacement in order to minimize the change of mechanical physical properties of the tracheal replacement and prevent internal absorption of the cartilage part in which cells may be comprised.

On the other hand, the framework of the tracheal replacement according to one embodiment of the present invention has a bellows shape in order to implement a mechanical behavior similar to the trachea in a human body. The bellows is a structure in which convolutions are made on the annular cylinder surface, and is a functional structure having larger resistance to compression and higher flexibility and patency, compared to the cylinder shape. The bellows framework has different flexibility depending on the number of convolutions per unit length, size of inclination angle, and wall thickness, and they can be modified according to the histological dimension of the actual trachea of a patient to be grafted.

More specifically, the bellows framework according to the present invention has composition which convolutions drawn to the outside in a longitudinal direction when shown on the outer side, and grooves entering the inside between the convolution and convolution are present on the outer side, as can be seen in FIG. 16. The inclination angle between the convolution and groove may be modified to 0° to 45°, and the longitudinal thickness of the groove may be 0 to 5 mm, for example, 4 mm which is same as the longitudinal thickness of the tracheal cartilage in a human body, and the length of the convolution may be 1 to 5 mm (no length of the convolution refers to a triangle convolution, and the minimum length in case of the triangle convolution is 2 mm), for example, 3 mm.

The bellows framework may be prepared without pores, and may be prepared as porous one having pores, but it is preferable to prepare it to have porosity for effective blood vessel formation and mucosal tissue regeneration, when grafted in a human body. The porous wall having pores according to one embodiment of the present invention may have the porosity of 50% or less, for example, 20 to 50%, and it may have pores having a diameter or side length of 260 to 300 on. The pores may be suitably adjusted by material dispensing/non-dispensing section (material dispensing ON/OFF) control, and controlling the transfer speed of the dispensing head in each section, intensity of air pressure, material dispensing speed (amount of the material dispensed for a unit time), and the like, when printing a material of the bellows framework.

The bellows framework may be prepared using a thermoplastic polymer, and the available thermoplastic polymer may be one or more kinds selected from the group consisting of polycaprolactone (PCL), poly(lactate-co-glycolate) (PLGA), poly lactic acid (PLA), polyurethane (PU) and poly(lactide-co-caprolactone) (PLCL), but not limited thereto, and preferably, it may be polycaprolactone (PCL). In particular, in case of polycaprolactone, it is dispensed at a relatively low temperature, it has high cell viability when printed together with cells, and therefore it is appropriate to use.

It is preferable to prepare the bellows framework of the present invention so as to have hydrophilicity, and for example, the contact angle with water may be 50° or less, or 20 to 50°. When the bellows framework has hydrophobicity, it has a great possibility that the cartilage part and epithelium part printed in the outer side and inner side of the framework are separated from the bellows framework in the in vitro culture process, and therefore it is necessary to increase the hydrophilicity of the bellows framework prepared with a material for preparation of the bellows framework. As one embodiment of the present invention, the bellows framework may be under plasma treatment, preferably oxygen plasma treatment so as to have hydrophilicity, and more specifically, as the result of dropping water drops on the surface of the framework and measuring the contact angle between the surface and water drops, after the plasma treatment of the bellows framework prepared with a thermoplastic polymer, for example, PCL, it was confirmed that the measured contact angle showed a numerical value of 50° or less.

The internal surface of the bellows framework of the tracheal replacement according to one embodiment of the present invention may consist of an epithelium part, in consideration that the internal surface of the actual trachea is covered with respiratory mucosal epithelium tissue, and it may comprise an annular cartilage part formed along the outer side groove of the bellows framework.

The cartilage part formed in the outer side groove of the bellows framework may use a non-biocompatible biomaterial polymer such as medical silicone, and the like, for preventing regeneration of tracheal cartilage tissue, that is, a material which has no harm in a human body when grafted and is not degraded in the human body, for the purpose of simply replacing cartilage without considering cartilage regeneration.

On the other hand, as a material of the epithelium part and cartilage part, a hydrogel polymer may be used, and if needed, one or more kinds selected from the group consisting of a cell and a growth factor may be further comprised. For example, the epithelium part and cartilage part may be a combination comprising (a) a hydrogel polymer, (b) a hydrogel polymer and a cell, (c) a hydrogel polymer and a growth factor, or (d) a hydrogel polymer, a cell and a growth factor.

The kinds of the hydrogel polymer used in the epithelium part and cartilage part may be possible to be selected in a wide range such as collagen, alginate, hyaluronic acid and decellularized tissue derived hydrogel, and the like.

As a cell which may be comprised in the hydrogel polymer of the epithelium part, various cells such as epithelial cells, stem cells, and the like, and combinations thereof are available, and the growth factor comprised in the epithelium part may be one or more kinds of growth factors effective in regeneration of mucosal tissue such as transforming growth factor beta 1 (TGF-β1), hepatocyte growth factor (HGF), keratinocyte growth factor (KGF), epithelial growth factor (EGF), epidermal growth factor (EGF), fibroblast growth factor (FGF), and insulin-like growth factor (IGF) and the like.

In addition, the hydrogel polymer of the cartilage part may comprise a growth factor effective for cell or cartilage regeneration, if needed. As a cell which may be comprised in the hydrogel polymer of the cartilage part, various cells such as chondrocytes, stem cells, and the like and combinations thereof are available, and a growth factor effective for regeneration of cartilage tissue may comprise a growth factor such as FGF, bone morphogenetic protein (BMP-2), transforming growth factor-β, TGF-β1, TGF-β2, TGF-β3, insulin, TGF-1, TGF-α, Osteolectin, IGF-1 or NGF, or the like.

Other one embodiment of the present invention provides a bellows framework and a preparation method of a tracheal replacement comprising the same using three-dimensional printing technology.

In general, the tracheal replacement prepared based on the three-dimensional printing technology may be divided into two methods depending on the use of a sacrificial layer. The first method is a method comprising printing a sacrificial layer in the printing process, and it can prepare a tracheal replacement by one-time printing process (See FIG. 3). In the first method, in the dispensing method of three-dimensional printing system, 4 dispensing heads are used. 4 kinds of materials in total are loaded in a syringe in the inside of the dispensing head, and each syringe may be heated to melt the internal material if needed. The material in the syringe may be dispensed through a nozzle at the syringe end using a physical force, for example, air pressure, a screw, or a plunger.

As shown in FIG. 3, when using a printing device having 4 dispensing heads in the present invention, a material for bellows framework printing (material #1) in dispensing head #1, a material for sacrificial layer printing (material #2) in dispensing head #2, a material for epithelium part printing (material #3) in dispensing head #3, and a material for cartilage part printing (material #4) in dispensing head #4 are loaded. As one specific example, as shown in FIG. 3, material #1 is dispensed at first (FIG. 3(A)), and then material #2 is dispensed in the same interval of the inside and outside of material #1 printed annularly (FIG. 3(B)). Material #1 and material #2 are dispensed at the same position and are laminated (FIG. 3(C)), and when they are laminated to a certain height, material #3 is dispensed once in the vacant space between material #1 and material #1 printed in the inside of material #1 (FIG. 3(D)).

Then, material #1 and material #2 are sequentially repeatedly dispensed again. Then, to prepare a bellows shape, material #1 is dispensed and laminated, and material #2 is continuously dispensed at the same position and is laminated in a cylinder shape (FIG. 3(E), (F)). When the dispensed material #1 and material #2 reach a certain height, material #3 is dispensed once in the vacant space between material #1 and material #2 printed in the inside of material #1, and material #4 is dispensed once in the vacant space between material #1 and material #2 printed in the outside of material #1 (FIG. 3(G)).

By the same method, through sequential dispensing and lamination of materials #1, #2, #3 and #4 (FIG. 3(H)~(L)), the structure such as FIG. 3(M) can be prepared. After that, by melting the sacrificial layer (material #2), the tracheal replacement such as FIG. 3(N) can be finally obtained.

The preparation of the tracheal replacement based on three-dimensional printing using a sacrificial layer according to the first method makes it possible to prepare the whole tracheal replacement by one time loading of materials. However, there are disadvantages that the printing process becomes complex by using 4 dispensing heads, and the printing time becomes longer as the size of the support increases, and the like. The extension of the printing time may lead necrosis of cells in the material loaded on the syringe in the inside of the dispensing head, and this may adversely affect reconstruction of the trachea using a support.

Therefore, other one embodiment of the present invention provides a preparation method of a tracheal replacement using three-dimensional printing technology without using dispensing and lamination of a sacrificial layer, which is a new preparation method divided into "printing process of a bellows framework" and "sequential printing process of an epithelium part and a cartilage part comprising cells".

In the second preparation method without using a sacrificial layer, at first a bellows framework is prepared using material #1 for preparing a bellows framework. The bellows framework may be prepared in a tubular shape, and may be prepared as a porous wall. It is preferable that the bellows framework is prepared as one having a porous wall for effective blood vessel formation and mucosal tissue regeneration, when the tracheal replacement is grafted in a human body, and for example, it may be prepared as one having pores of 260~300 µm, or one having porosity of 20~50%.

More specifically, a porous bellows framework having pores may be prepared by variably controlling the movement speed of the dispensing head when dispensing a material (dispensing section) and not dispensing it (non-dispensing section). The variable speed control means making structural properties by making a difference between the speed when dispensing a material and the speed when not dispensing a material. In other words, for making the outer wall, the dispensing head should move at A speed while dispensing a material, and for forming pores in the middle, it should move at B speed with stopping dispensing a material, to form a porous framework. For example, as shown in FIG. 4, by controlling the movement of the dispensing head and the movement speed, and the dispensing of the material, when printing material #1, for the porous bellows framework, a porous conduit type of bellows framework may be prepared. The dispensing head of a three-dimensional printer dispenses material #1 for printing of the bellows framework and moves at a certain speed (FIG. 4(A)), and moves at a rapid speed for a certain section while dispensing is stopped (FIG. 4(B)). Then, material #1 remained at the end of the head nozzle forms a filament and loosed, and an empty interval is made in the middle part of the moving section. Then, when the head is transferred while dispensing material #1 at a certain speed again (FIG. 4(C)), a dotted line form is prepared, and by laminating it, a porous hollow wall type of structure may be prepared. Then, proses are formed in the middle part of the section where the dispensing head transfers it at a rapid speed.

The method of preparing a porous bellows structure having pores, by variably controlling the movement speed of the dispensing head in the dispensing section and non-dispensing section of the dispensing head material with a 3D printer, is not limited only to preparation of a bellows framework, but it may be used for preparing various porous tubular structures in addition to the bellows framework.

As a method of preparing a bellows framework using three-dimensional printing technology according to one embodiment of the present invention, preferably, the bellows framework may have a porous and/or concave-convex structure having pores. The method of preparing a bellows framework may comprise (a) preparing a thermoplastic polymer solution melt by inputting a thermoplastic polymer into a syringe and heating; and (b) dispensing the thermoplastic polymer through a dispensing head nozzle of a three-dimensional printer by applying a physical force.

As a method of preparing an artificial tracheal replacement using three-dimensional printing method according to additional one embodiment of the present invention, in addition to the step of preparing a bellows framework, it further comprises preparing an annular cartilage part by printing a bio-ink for forming a cartilage part along the circumference of grooves on the outer side of the bellows framework, and preparing an epithelium part by printing a bio-ink for forming an epithelium part on the inner side of the bellows framework. The annular cartilage part is prepared by printing a bio-ink for forming a cartilage part along the circumference of concave-convex grooves on the outer side of the bellows framework, and the epithelium part is prepared by printing a bio-ink for forming an epithelium part on the inner side of the bellows framework. The preparation of a cartilage part and preparation of an epithelium part may be carried out simultaneously or sequentially.

According to one embodiment of the present invention, the method of preparation of a bellows framework using three-dimensional printing technology and the method of preparation of an artificial tracheal replacement will be described in more detail by each step.

(1) Step of Preparation of a Bellows Framework

It is a step of preparing a bellows framework according to the preparation method of the present invention, it can prepare a porous bellows framework having a concave-convex structure, by performing (a) preparing thermoplastic polymer melts by inputting a thermoplastic polymer into a syringe and heating; and (b) dispensing the thermoplastic polymer through a dispensing head nozzle of a three-dimensional printer by applying a physical force, for example, air pressure, screw or plunger.

Additionally, various treatment processes, which can improve material, structural and mechanical physical properties and the like of the bellows framework obtained by the preparation method, may be further performed, and for example, at least a process selected from the group consisting of heating treatment and oxygen plasma treatment processes may be performed. In addition, the order of the heating treatment and oxygen plasma treatment of the bellows framework may be done in reverse order, and it is not necessary to perform the oxygen plasma treatment after heating treatment.

The thermoplastic polymer of the above step is filled into a syringe, and then melts obtained by heating to 60 to 200° C., preferably 65 to 90° C. are dispersed and printed, and when dispersing, the melts dispersing section and non-dispersing section are set and this is repeatedly printed, and thereby a bellows framework having porosity may be prepared. More specifically, by controlling the movement speed of the dispersing head in the dispersing section of melts of the thermoplastic polymer, the thickness of the porous bellows is controlled, and by controlling the movement speed of the dispersing head in the non-dispersing section, the size and porosity of pores are controlled.

The dispersing of the melts may be carried out at a movement speed of 60 to 150 nm/min, preferably 70 to 100 nm/min, for example 80 to 90 nm/min, by applying an air pressure of 400 to 600 kPa, and the distance of non-dispersing section that is a pore-forming section (B section in FIG. 4) is 300 to 800 µm, preferably 400 to 700 µm, for example, 600 µm, and the distance between non-dispersing sections is 100 to 1000 µm, and the dispersing head is moved at a movement speed of 200 to 600 mm/min without dispersing melts to form pores. When pores are formed under the above condition, pores are neatly and densely formed best.

More specifically, to prepare a porous bellows framework, a thermoplastic polymer is inputted to a syringe and is melted by heating treatment, and then materials are dispersed through a nozzle at the end of the syringe using a physical force, for example, air pressure, screw or plunger, and when dispersing materials, dispersing and non-dispersing are repeatedly performed to form a gap. For example, as shown in Example 1, after melting PCL to 60 to 100° C. to make it in a melted state, materials are dispersed at an air pressure of 400 to 600 kPa, for example, 500 kPa, at a dispersing speed of 80 to 90 mm/min, for example, 85 mm/min, and in the section in which the head is transferred without material dispersing, pores may be formed by transferring the distance of 100 to 600 µm at 305 to 505 mm/min without material dispersing. When preparing by the above method, pores are densely formed best (See FIG. 5).

As described above, a bellows framework may be prepared using a lamination method of a dispersing method of three-dimensional printing technology, but the bellows framework prepared by the method has a relatively weak bonding force between laminated layers. Thus, to achieve the complete structural integrity such as the structure prepared by the molding method, it is preferable to add a heating treatment process, between the process of preparing a bellows framework and the process of printing an epithelium part and/or a cartilage part.

The heating treatment process may be performed by treatment for a certain time under the same temperature as the melting point of the material of the prepared bellows framework (incubation), and more specifically, it is suitable to treat in a range of 40 to 200° C., preferably, 50 to 70° C., more preferably, 55 to 65° C., for example, 60° C. In case of the reaction time, it is suitable to treat for 10 minutes to 60 minutes, preferably 20 to 50 minutes, more preferably 20 minutes to 30 minutes. In particular, as shown in FIG. 8, when the heating treatment is performed at 60° C. for about 25 minutes, in the three-point bending test, the difference between distance-weight diagram is shown the smallest, and therefore, it can be confirmed that excellent structural integrity physical properties can be obtained, when preparing a bellows framework under the above condition.

In addition, as hydrophilic treatment of the bellows framework, in case of the oxygen plasma treatment process, the treatment condition may be modified flexibly depending on the size, shape, use, and the like of the bellows framework. For example, the bellows framework may be inputted to a plasma cleaner of 50 to 150 W, for example, 100 W, at a room temperature, and the reaction may be performed for about 30 minutes to 3 hours, for example, 1 hour to 2 hours. In addition, when a process of turning over the position of the bellows framework up and down for the reaction time is performed once or more, the surface hydrophilicity may be effectively improved in the same time, than the case of not modifying the position of the framework. When performing the oxygen plasma treatment process under the above condition, as shown in the following Example 3 and FIG. 9 and FIG. 10, the contact angle of the surface measured by a measuring instrument of contact angle with water is 50 degree or less, and therefore the surface hydrophilicity of the framework can be improved most excellently.

In order that the final printed tracheal replacement is stably grafted in the trachea in a human body after in vitro culture for a certain time, the epithelium part and the cartilage part should be maintained in the printed position well, without being separated from the bellows framework. Separation of the epithelium part and the cartilage part from the bellows framework depends on the hydrophilicity and hydrophobicity of the material for preparing a bellows framework. If a bellows framework prepared by a material for preparing a bellows framework has hydrophobicity, there is a great possibility for the printed epithelium part and the cartilage part to be separated from the bellows framework in the in vitro culturing process, and thus it is preferable to increase the hydrophilicity of the bellows framework prepared by the material for preparing a bellows framework if necessary.

(2) Step of Preparation of a Cartilage Part and/or an Epithelium Part

In the method for preparation of an artificial tracheal replacement according to the present invention, the step of preparing a cartilage part or an epithelium part, may be performed by printing bio-ink for forming a cartilage part along the circumference of grooves on the outer side of the bellows framework to prepare an annular cartilage part, and printing bio-ink for forming an epithelium part on the inner side of the bellows framework to prepare an epithelium part. For printing bio-ink, it may be performed by inputting the bio-ink to a syringe and applying a physical force and dispersing it through a dispersing head nozzle of a three-dimensional printer. The physical force, for example, air pressure, screw or plunger may be used.

The step of preparing a cartilage part or an epithelium part according to one example of the present invention may prepare by printing bio-ink under the condition of an air pressure of 20 kPa to 200 kPa, preferably, 30 kPa to 150 kPa, and a rotation speed of 3 to 180 DPS, preferably, 4.5 to 33 DPS (degree per second), and it may further perform a process for forming cross-linking, after printing bio-ink. The kinds of the process for forming cross-linking is not particularly limited, and a suitable process may be used depending on the kinds of the used bio-ink. For example, when using collagen or decellularized tissue derived hydrogel as bio-ink, cross-linking may be formed by a heating treatment process.

In case of printing of a cartilage part, a hydrogel polymer comprising cells may be used as bio-ink, and in general, the higher the amount of cells and the concentration of the hydrogel polymer comprised in bio-ink are, the higher the viscosity of bio-ink is. As the viscosity of bio-ink is higher, the air pressure to disperse it may be increased. In addition, in case of a curved nozzle used in printing a cartilage part, it may be selected differently according to the size of a tracheal replacement to be prepared, for example, for a rabbit animal experiment and for a dog animal experiment, and the like, and the internal diameter of the curved nozzle may be 0.15 to 1.52 mm. The smaller the internal diameter of the curved nozzle is, the higher the air pressure to disperse bio-ink is, and the air pressure used for dispersing bio-ink may be 30 to 150 kPa, preferably, 50 to 120 kPa. In addition, the more the amount of bio-ink dispersed per unit time is, the rotation speed of the bellows framework increase, and this may be 4 to 35 DPS (Degree per Second), for example, 4.5 to 33 DPS. Specifically, as shown in Example 4, when bio-ink is dispersed at the air pressure of 60 kPa and the rotation speed of 9 to 10.5 DPS, or at the air pressure of 70 kPa and the rotation speed of 25.5 to 27 DPS, the printed cartilage part material is contracted to the volume of the outer grooves of the bellows framework, and therefore, it can be seen that the above range is an appropriate condition of cartilage part printing.

In case of printing an epithelium part, it is preferable to use a curved nozzle, and the internal diameter of the curved nozzle may be 0.15 to 1.52 mm. The air pressure used to disperse bio-ink may be 20 kPa to 200 kPa, preferably, 30 to 150 kPa, more preferably, 50 to 120 kPa, and the smaller the internal diameter of the curved nozzle is, the air pressure to disperse bio-ink increases. In addition, the rotation speed of the bellows framework may be 3 to 180 DPS (degree per second), and the more the amount of bio-ink to be dispersed is, the rotation speed of the bellows framework increases. In case of the present invention, to print an epithelium part material to internal grooves of the bellows framework, the same condition as printing of the cartilage part (air pressure of 120 kPa) is used (See FIG. 14), and to print an epithelium part material on the internal surface other than the internal grooves, a rotation speed twice faster than the condition of printing the cartilage part is used.

The bio-ink used in printing an epithelium part and a cartilage part may comprise a hydrogel polymer, and for example, it may be a hydrogel polymer of 0.5 to 5% by weight, and the hydrogel polymer may be one or more kinds selected from the group consisting of alginate, hyaluronic acid and decellularized tissue derived hydrogel. The hydrogel polymer is preferably biocompatible.

In addition, the bio-ink may further comprise one or more kinds selected form the group consisting of a cell and a growth factor. In case of the epithelium part, if needed, epithelial cells, stem cells or a mixture thereof and a mucosal tissue regeneration growth factor may be comprised, and in case of the cartilage part, chondrocytes, stem cells or a mixture thereof and a bone tissue growth factor may be comprised.

More specifically, when using hydrogel comprising cells as bio-ink, the concentration of the hydrogel material may be 0.5 to 5%, and the concentration of cells may be $1\times10^5$ to $5\times10^7$/ml. When comprising a growth factor in bio-ink for three-dimensional printing for forming an epithelium part, the concentration of the growth factor may be 10 to 500 ng/ml.

On the other hand, depending on the use of the cartilage part, a non-biocompatible polymer not comprising cells, for example, medical silicon may be used.

(3) Preparation of the Absorption Prevention Part of Cartilage Part

According to other one example of the present invention, the preparation method may further comprise preparing an absorption prevention part of cartilage part on the outer side of the cartilage part by three-dimensional printing technology, and the absorption prevention part of cartilage part may be prepared by printing by dispersing melts, which a thermoplastic polymer which is degraded in a living body is heated and melted to 60° C. to 200° C., at an air pressure of 400 to 600 kPa, and laminating at least one printing layer having a thickness of 80 to 200 μm, more preferably, 80 to 120 μm.

The cartilage part of the tracheal replacement according to the present invention is an exposed form as located between convolutions of the outer side of the trachea. Accordingly, the cartilage part consists of hydrogel and cells or growth factors, not a non-biocompatible biomaterial, there is a very high possibility that the tracheal replacement is absorbed in a body after grafted in a human body, before the cartilage is regenerated into a tracheal cartilage. Therefore, to prevent internal absorption of the cartilage part, it is preferable to equip an absorption prevention part of cartilage part which can surround the outer surface of the tracheal replacement.

Then, it is preferable that the absorption prevention part of cartilage part prevents internal absorption of the cartilage part effectively and at the same time, has porosity not to interrupt regeneration of the cartilage part to the tracheal cartilage, and in order to the absorption prevention part of cartilage part can be absorbed in a body after the cartilage part is regenerated to the tracheal cartilage, it is suitable to prepare it with a biocompatible material. In addition, it is preferable not to interrupt mechanical movement properties of the tracheal support, and therefore the absorption prevention part of cartilage part in the present invention may have a specific pattern such as stent which is used in vasodilation.

The absorption prevention part of cartilage part may be prepared in a membrane type, or a hollow cylinder form, depending on the method to be printed, and may be used together with the tracheal replacement. In case of the absorption prevention part of cartilage part prepared in a membrane type, it may be treated by a method of surrounding the cartilage part of the tracheal replacement, after grafting of the tracheal replacement, and in case of the absorption prevention part of cartilage part prepared in a hollow cylinder form, sealing of the tracheal replacement may be carried out after being combined to the tracheal replacement in advance. In other words, it is better to use the membrane type of absorption prevention part of cartilage part when partially using the tracheal replacement as a cut form, and the hollow cylinder form of absorption prevention part of cartilage part when using the whole one.

More specifically, when preparing the absorption prevention part of cartilage part in a membrane type or a tubular form, melts may be dispersed while drawing a stent pattern on a plane when dispersing them through a nozzle, and the tubular form of absorption prevention part of cartilage part may be printed and prepared, by dispersing PCL in a melted state in a longitudinal direction of the rotation axis according to a code for preparation of a cartilage part absorption inhibitor, and at the same time, stopping and rotating the rotation axis according to a code for forming a stent type of pattern, and dispersing the second pattern on the first pattern by dispersing PCL to laminate two layers, or three layers by 100 μm per layer.

Advantageous Effects

In the present invention, the three-dimensional tracheal replacement is a new type of support considering mechanical•biological properties of respiratory organs in a human body. In that it can copy flexibility and patency that are mechanical properties of respiratory organs in a human body intactly based on the bellows framework, and therefore it can minimize side-effects after surgery due to differences of mechanical properties between organs in a human body and grafted support after transplantation, and can effectively maintain the stability of a patient to which a tracheal support is grafted, and can achieve complete reconstruction of respiratory organs in a human body by considering simultaneous regeneration of a respiratory mucous epithelium and a tracheal cartilage, it can provide a new customized medical instrument which can overcome limitations of conventional supports used in tracheal reconstruction and can treat intractable tracheal defects fundamentally.

In addition, the method of preparing a three-dimensional tracheal replacement in the present invention can effectively secure the survival and functions of cells used in printing by shortening time used in a printing process of cells to a minimum, differently from the conventional printing method, and this can maximize the performance of the three-dimensional tracheal replacement, and thus it can provide a tracheal replacement which copies mechanical•biological properties of respiratory organs in a human body intactly.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 1 is a drawing which shows a tubular frame structure of the trachea of a human body.

FIG. 2 is a drawing which shows a tracheal replacement for reconstruction of extensive circular defects of the trachea according to one example of the present invention.

FIG. 3 is a schematic diagram which illustrates a process of preparing a tracheal replacement using a sacrificial layer according to one example of the present invention.

FIG. 4 is a schematic diagram which illustrates a 3D printing process for preparation of a hollow type of porous bellows structure without using a sacrificial layer according to one example of the present invention.

FIG. 5 shows the effect on pore formation according to changes of the temperature of PCL, the transfer speed of the dispensing head, and the length of B section according to one example of the present invention.

FIG. 6 shows the effect on pore formation according to the change of the distance between B sections according to one example of the present invention.

FIG. 7 shows a PCL bellows framework of two dimensions considering preclinical evaluation according to one example of the present invention.

FIG. 8 is a drawing which shows the flexural behavior of the bellows framework according to the change of time of heating treatment at 60° C. according to one example of the present invention.

FIG. 9 is a drawing which shows the effect of oxygen plasma treatment for surface hydrophilicity of the hollow type of rectangular PCL structure in a size of 8×8×13 mm prepared as a rabbit model according to one example of the present invention.

FIG. 10 is a drawing which shows the effect of oxygen plasma treatment for surface hydrophilicity of the hollow type of rectangular structure in a size of 18×18×33 mm prepared as a dog model according to one example of the present invention.

FIG. 11 is an approximate schematic diagram of the method for preparing an artificial tracheal replacement using the three-dimensional printing technology of the present invention. The step of preparation of the bellows support and the step of preparation of the cartilage and epithelium parts are separated from each other, and heating treatment or oxygen plasma treatment for enhancing physical properties of the bellows structure may be performed therebetween.

FIG. 12 shows photographs of cartilage part samples undergoing rotary printing in outer grooves of the PCL bellows framework prepared according to one example of the present invention.

FIG. 13 is a drawing which shows the contraction of the cartilage part at the first day after printing according to one example of the present invention.

FIG. 14 is a drawing which shows the epithelium part undergoing rotary printing (A) and the epithelium part at the third day after printing (B) according to one example of the present invention.

FIG. 15 is the result of the animal experiment for verifying the membrane type of absorption prevention part of cartilage part prepared according to one example of the present invention and its effect.

FIG. 16 is a drawing which shows the inclination angel of bellows framework convolutions, and the length of grooves, and the part of the length of convolutions.

FIG. 17 shows the numerical values as a graph, by comparing relative expression levels of factors related to cartilage differentiation (COL2, ACAN, SOX9) in each group through PCR, after preparing a bellows framework in which each cartilage part is printed by dispensing bio-ink having 4 kinds of cell density ($1\times10^6$/ml (Group I), $2\times10^6$/ml (Group II), $5\times10^6$/ml (Group III), $1\times10^7$/ml (Group IV)) to outer grooves of the PCL bellows framework.

FIG. 18 shows the numerical values as a graph, by comparing relative expression levels of factors related to mucosal tissue differentiation (MUSIN 5AC, KARATIN 14, BETA-TUBULIN) in each group through PCR, after preparing a bellows framework in which each epithelium part is printed by dispensing bio-ink having 4 kinds of cell density ($1\times10^6$/ml (Group I), $2\times10^6$/ml (Group II), $5\times10^6$/ml (Group III), $1\times10^7$/ml (Group IV)) to internal surfaces of the PCL bellows framework.

DETAILED DESCRIPTION OF THE INVENTION

The present invention will be described in more detail by the following examples, but the scope of the present invention is not intended to be limited by the following examples.

Example 1: Test of Conditions of Preparation of a Porous Bellows Framework

In the present invention, for preparation of a porous bellows framework, PCL was used. A certain amount (15~1,000 mg) of PCL was loaded in a 10 cc stainless syringe in the inside of the dispensing head, and the syringe was heated to 65~80° C., to melt PCL. The melted PCL was made to be dispensed through a metal nozzle (N20, inner diameter: 200 μm, Musashi Engineering) at the end of the syringe at an air pressure of 500 kPa. After fixing the height of PCL laminating to 100 μm (three layers in total), and the speed of dispensing PCL in sections A and C to 85 mm/min, the formation of pores was observed according to changes of the temperature of PCL, the distance of B section, and the transfer speed in this section (305, 405 and 505 mm/min) (FIG. 5).

As the result of the experiment, it was confirmed that the pores were formed best, when the temperature of melting PCL to 80° C., and the distance of B section to 600 μm, and the transfer speed of the dispensing head in the B section to 305 mm/min. In case of the transfer speed of the dispensing head, there was no big difference in three conditions (305, 405 and 505 mm/min), and to minimize vibrations of the head occurring when the dispensing head transfers rapidly, it is better to select the smallest transfer speed (305 mm/min).

Then, the experiment about how much densely the pores were formed when PCL was loaded as three layers at a height of 100 μm under the established conditions was carried out. The distance of B section of transferring at a speed of 305 mm/min without dispensing PCL was fixed to 600 μm, and the distance between B sections was changed to 100~600 μm, and the formation of pores was observed (FIG. 6).

As the result of the experiment, it was confirmed that the pores were formed well until the distance between B sections was 100 μm at a minimum. Accordingly, pores can be formed at an interval of at least 400 μm in the hollow wall type of structure. This means that the porosity of the bellows framework can be controlled if needed.

In the present experiment, bellows frameworks of two dimensions were prepared in consideration of preclinical evaluation of the tracheal replacement (animal experiment using rabbit and beagle dog) (FIG. 7). As a result, in the present invention, a bellows framework having various dimensions and porosity as necessary can be prepared by three-dimensional printing technology of the dispensing method.

Example 2: Evaluation of Structural Integrity of the Bellows Framework (Heating Treatment)

In the present experiment, a bellows framework was prepared using PCL, and the melting point of PCL was 60° C. Therefore, for heating treatment of the prepared bellows framework, the internal temperature of a vacuum oven (OV-11, JEIOTECH, Korea) was set to 60° C., and for heating treatment, the bellows framework was stored in the oven for 10~30 minutes. After that, to evaluate the structural integrity of the bellows framework undergoing heating treatment under each condition, the three-point bending test was performed. In the three-point bending test, to apply bending to the bellows framework, it was conducted by supporting the convolution part at both ends of the bellows framework and pressing the central part between convolutions at both ends (the part in the middle of the bellows framework in a longitudinal direction). In addition, the size of load occurring by pressing the central part of the bellows framework and applying bending was observed.

As shown in FIG. 8, as the time of heating treatment increases, the displacement point at which the bellows framework causes rupture under bending increases. In addition, it can be seen that the condition of heating treatment at 60° C. for 25 minutes is the most effective. Furthermore, it can be confirmed that the difference of the distance-load diagram of each sample under the condition of heating treatment for 25 minutes is the smallest.

Example 3: Evaluation of Hydrophilicity of the Bellows Framework (Hydrophilicity Treatment)

When the bellows framework is hydrophobic, it is a great possibility that the printed epithelium part and cartilage part are separated from the bellows framework in the process of in vitro culture, and therefore, it is needed to increase the hydrophobicity of the bellows framework prepared with material 1 if needed. In the above Example 2, PCL was used in preparation of the bellows framework, and this material has the very high hydrophobicity. Thus, the hydrophilicity of the surface of the bellows framework was increased through a process of oxygen plasma treatment.

At first, considering the preclinical evaluation of the tracheal replacement (animal experiment using rabbit and dog), rectangular cylinder structures of two kinds of dimensions were prepared. In addition, the rectangular cylinder structures prepared using Plasma Cleaner (PDC-001, Harrick Plasma) were subjected to oxygen plasma treatment under each condition (Group I: 100 W+30 minutes treatment, Group II: 100 W+60 minutes treatment, Group III: 100 W+30 minutes treatment+overturning the top and bottom of the structure and then 30 minutes treatment, Group IV: 100 W+60 minutes treatment+overturning the top and bottom of the structure and then 60 minutes treatment). Then, the contact angle at each position (A, B) in the internal and outer surfaces was measured to verify the effect of oxygen plasma treatment (FIG. 9).

In the rectangular cylinder structure of 8×8×13 mm considering the dimension for the rabbit animal model, the longer the oxygen plasma treatment is carried out, the better the hydrophilicity in the internal and outer surfaces becomes (FIG. 9, Groups I and II). In addition, in the same treatment time, by comprising the process of overturning the positions of the top (A) and the bottom (B) of the structure between treatment, the uniformity of the surface hydrophilicity of the total structure is raised (FIG. 9, Groups II and III). However, there is no big difference between oxygen plasma treatment for one hour and two hours (FIG. 9, Groups III and IV), it can be concluded that the oxygen plasma treatment for 1 hour including the process of replacing the positions of the top 9A) and the bottom (B) of the structure (100 W+30 minutes treatment+overturning the top and the bottom of the structure and then 30 minutes treatment) is the most effective (FIG. 9, Group III).

In case of the rectangular cylinder structure in a size of 18×18×33 mm considering the dimension for the dog animal model, as the result of observing the internal and outer surface hydrophilicity in the top, middle and bottom parts of the structure, it could be confirmed that the condition of plasma treatment for 2 hours in Group 11 (100 W+60 minutes treatment+overturning the top and the bottom of the structure and then 60 minutes treatment) had an excellent effect of improving the cylinder surface hydrophilicity than the condition of plasma treatment for 1 hour in Group I (100 W+30 minutes treatment+overturning the top and the bottom of the structure and then 30 minutes treatment) (FIG. 10, Groups I and II).

In this way, by adding the heating treatment and oxygen plasma treatment processes of the bellows framework between the printing process of the bellows framework and the printing process of the epithelium par and the cartilage part, the structural integrity and surface hydrophilicity of the bellows framework prepared earlier were increased. Such an additional treatment process is possible by separating the printing process of the bellows framework and the printing process of the epithelium part and the cartilage part, and therefore it can be added or skipped depending on physical properties of the bellows framework material.

Example 4: Printing the Cartilage Part of the Artificial Trachea

Then, the printing process of the cartilage part and the epithelium part is followed. This printing process uses a motorized rotation stage and a curved nozzle (FIG. 11). At first, the prepared bellows framework is on the rotation stage for printing of the cartilage part, and the dispensing head equipped with the cartilage part material moves, and the end of the curved nozzle is positioned at the outer groove part of the bellows framework. In addition, the bellows on the stage is rotated together as the rotation stage is rotated at a certain speed at the same time when the cartilage part material starts to be dispensed. When the bellows framework rotates 360°, the rotation stage stops to rotate, and at the same time, dispensing the cartilage part material is terminated together. Then, the dispensing head moves and the end of the curved nozzle is positioned at other groove part of the bellows framework, and the material is dispensed and the bellows framework rotates 360°. Such a process is repeated until the cartilage part material is filled in all the outer groove parts of the bellows framework.

As the cartilage material, liquid collagen including human septal chondrocytes (hNSCs) (3% atelocollagen, Therafill, Sewon Cellontech., Seoul, Korea) was used. To secure a sufficient cell number ($1 \times 10^7 \sim 1 \times 10^8$/ml), hNSCs were cultured in vitro in a DMEM culture solution containing 10% fetal bovine serum (FBS) for a certain period, and the culture solution (cell suspension) including hNSCs was mixed with the liquid collagen at a volume ratio of 1:10 so as to have a cell density of $1 \times 10^7$/ml, to prepare bio-ink. After loading the prepared bio-ink in a syringe in the dispensing head, it was dispensed through a curved nozzle (CPN-25G-A45, inner diameter: 250 μm, Musashi Engineering). Then, the appropriate cartilage part printing condition was established in the range of the air pressure of 50~120 kPa and the rotation speed of 4.5~33 DPS (degree Per Second).

As shown in FIG. 12, the cartilage part material was successively printed in the outer groove of the bellows framework in the various air pressure and rotation speed ranges. It was confirmed that the cartilage part material was flowed down in the air pressure of 70 kPa and the rotation speed of 9 DPS, but it was confirmed that in other conditions, the printed cartilage part material was not flowed down even when dispensing a larger amount of cartilage part materials than the volume of the original outer groove, and it was remained well in the outer groove of the bellows framework.

The bellows framework in which the cartilage part was printed was incubated at 37° C. for about 30 minutes and then was cultured in a 37° C., 5% $CO_2$ incubator overnight, for cross-linking of collagen. In this process, it was confirmed that the contraction of the printed cartilage part material occurred (FIG. 13) and the cartilage part material printed under the condition of the air pressure of 60 kPa and 10.5 DPS and 9 DPS, and the air pressure of 70 kPa and 27 DPS and 25.5 DPS was contracted to the volume of the outer groove of the bellows framework. Accordingly, in consideration of the level of contraction of the printed cartilage part and the printing time, it can be concluded that the printing condition using the air pressure of 70 kPa and the rotation speed of 25.5 DPS is the most suitable.

In addition, bio-ink was prepared by the same method as above using another collagen used in the clinic (3% atelocollagen, UBIOSIS, Korea), and the cartilage part printing experiment was progressed. The cartilage part printing when using another collagen was performed under the condition of the air pressure of 120 kPa and 12 DPS. (Even if the same collage, if using a different manufacturer's product, the printing condition will be different.)

Example 5: Printing of the Epithelium Part of the Artificial Trachea

Then, the printing process of the epithelium part of the internal surface of the bellows. The end of the curved nozzle of the dispensing head equipped with the epithelium part material is positioned at the groove part in the inside of the bellows framework, and as same as the cartilage part material is printed, the epithelium part material is dispensed and at the same time, the stage rotates 360°. In this way, after the epithelium part material is filled in all the internal groove parts of the bellows framework, the epithelium part material is filled on the surface between the internal groove and groove in the same way.

In the present invention, as the epithelium part material, collagen including human nasal inferior turbinate derived mesenchymal stem cells (hTMSCs) was used. To secure a sufficient cell number ($1 \times 10^6 \sim 1 \times 10^7$/ml), hTMSCs which were cultured in vitro in a DMEM culture solution containing 10% fetal bovine serum (FBS) for a certain period were mixed with 3% liquid collagen and were loaded in the syringe in the dispensing head, and then were dispensed through the curved nozzle. To print the epithelium part material in the internal groove of the bellows framework, the condition as same as printing of the cartilage part was used (FIG. 14), and to print the epithelium part material on the other internal surface except for the internal groove, the rotation speed two times faster than the printing condition of the cartilage part was used.

Example 6: Printing of the Absorption Prevention Part of Cartilage Part of the Artificial Trachea 6-1. Printing of the Membrane Type of Absorption Prevention Part of Cartilage Part Following Example 5, to prevent the internal absorption of the printed cartilage part, printing of the absorption prevention part of cartilage part can be followed. In the present invention, to prepare a membrane type of absorption prevention part of cartilage part, PCL was used. PCL in a certain amount (15~1,000 mg) was loaded in the 10 cc stainless syringe in the inside of the dispensing head, and the syringe was heated to 65~80° C., to melt PCL. The melted PCL was made to be dispensed through a metal nozzle (N20, inner diameter: 200 μm, Musashi Engineering) at the end of the syringe at the air pressure of 500 kPa. The membrane is dispensed as drawing a certain pattern so as to have the same pattern with stent when surrounding the tracheal replacement, and this is printed in two layers, or three layers. Then, the second pattern is drawn while dispensing PCL on the first pattern, and this is also printed in two layers or three layers. The height of loading PCL is 100 μm (FIG. 15(A)).

The membrane type of the absorption prevention part of cartilage part was prepared, and the level of cartilage part absorption of the tracheal replacement according to its application was verified through an experiment using a nude mouse. The animal experiment using the nude mouse was performed for two months in total, and the level of absorption of the cartilage part was observed by extracting the tracheal replacement at the first month and second month after grafting the tracheal replacement subcutaneously in the nude mouse. It was confirmed that in case of the tracheal replacement applying the absorption prevention part of cartilage part (Group II), the volume of the cartilage part printed initially was maintained well. However, it could be seen that the cartilage part was significantly absorbed and the volume of the cartilage part was significantly reduced, when grafting only the tracheal replacement without the absorption prevention part of cartilage part to the nude mouse subcutaneously (Group I) (FIG. 15(A)).

6-2. Printing of a Tube Type of Absorption Prevention Part of Cartilage Part

To prepare a tube type of absorption prevention part of cartilage part, PCL was used. PCL in a certain amount (15~1,000 mg) was loaded in the 10 cc stainless syringe of the inside of the dispensing head, and the syringe was heated to 65~80° C., to melt PCL. The melted PCL was dispensed through a metal nozzle (N20, inner diameter: 200 µm, Musashi Engineering) at the end of the syringe at the air pressure of 500 kPa. The syringe was positioned on the rotation axis according to the initial position set in advance, and for preparation of the tube type, PCL was dispensed in a longitudinal direction of the rotation axis according to the code. At the same time, for forming a stent type of pattern, the rotation axis was stopped and rotated according to the code. Then, the second pattern was made by dispensing PCL on the first pattern, and it was printed in two layers or three layers. Each height at which PCL is laminated is 100 µm.

Example 7: Cell Content of the Cartilage Part and the Epithelium Part

In printing of the cartilage part and the epithelium part, chondrocytes, stem cells and the like which facilitates cartilage formation as the cartilage part material can be comprised, and mucosal cells, stem cells and the like as the epithelium part material can be comprised. In this case, at first, to carry out rotary printing of the cartilage part and the epithelium part of the tracheal replacement, securing a sufficient amount of cell number is necessary, and since the effect of tissue regeneration of the cartilage part and the epithelium part can be affected depending on the concentration of cells comprised in the printed cartilage part or epithelium part, it is needed to determine the optimal content of cells showing the most excellent tissue regeneration effect while considering the rotary printing efficiency.

Accordingly, to determine the optimal content of stem cells comprised in the cartilage part and epithelium part, the following experiment was carried out.

7-1. Determination of the Optimal Cell Content of the Cartilage Part of Tracheal Replacement To secure a sufficient cell number ($1\times10^6$~$1\times10^7$/ml), hNSCs (Human neural stem cells) which were cultured in vitro in a DMEM culture solution containing 10% fetal bovine serum (FBS) for a certain period were mixed with 3% liquid collagen, to prepare bio-ink having 4 kinds of cell density in total ($1\times10^6$/ml (Group I), $2\times10^6$/ml (Group II), $5\times10^6$/ml (Group III), $1\times10^7$/ml (Group IV)). After loading the prepared bio-ink in the syringe in the inside of the dispensing head, it was dispensed to the outer groove part of the PCL bellows framework through the curved nozzle. In this experiment, the PCL bellows framework having only one outer groove was used.

The bellows framework of which cartilage part was printed was cultured in a 37° C., 5% $CO_2$ incubator for one week, after keeping it at 37° C. for about 30 minutes for cross-linking of collagen. Then, the DMEM culture solution containing 10% fetal bovine serum (FBS) was newly replaced per 2~3 days. After that, to confirm the effect of cartilage regeneration by each cell content, the expression levels of each factor related to cartilage differentiation (COL2, ACAN, SOX9) were compared by polymerase chain reaction (PCR), and then, the expression levels of each factor related to cartilage differentiation were represented by relative values to the expression of GAPDH which was used as a control gene (See FIG. 17).

As shown in FIG. 17, as the result of comparing the relative values of factors related to cartilage differentiation by each group (Group I to Group IV), it was shown that the expression was highest in the group printed with the bio-ink having the cell content of $2\times10^6$/ml (Group II). Therefore, it could be seen that it was most suitable to comprise the cell content of $2\times10^6$/ml, when using bio-ink comprising hNSCs, in preparation of the tracheal replacement support by printing the cartilage part on the porous bellows surface of the present invention.

7-2. Determination of the Optimal Cell Content of the Epithelium Part of the Tracheal Replacement To secure a sufficient cell number ($1\times10^6$~$1\times10^7$/ml), hTMSCs (Human turbinate mesenchymal stromal cells) which were cultured in vitro in a DMEM culture solution containing 10% fetal bovine serum (FBS) for a certain period were mixed with 3% liquid collagen, to prepare bio-ink having 4 kinds of cell density in total ($1\times10^6$/ml (Group I), $2\times10^6$/ml (Group II), $5\times10^6$/ml (Group III), $1\times10^7$/ml (Group IV)). After loading the prepared bio-ink in the syringe in the inside of the dispensing head, it was dispensed to the outer groove part of the PCL bellows framework through the curved nozzle. In this experiment, the PCL bellows framework having only one outer groove was used.

The bellows framework of which epithelium part was printed was cultured in a 37° C., 5% $CO_2$ incubator for one week, after keeping it at 37° C. for about 30 minutes for cross-linking of collagen. Then, the DMEM culture solution containing 10% fetal bovine serum (FBS) was newly replaced per 2~3 days. After that, to confirm the effect of mucosal tissue regeneration by each cell content, the expression levels of each factor related to mucosal tissue differentiation (MUSIN 5AC, KARATIN 14, BETA-TUBULIN) were compared by polymerase chain reaction (PCR). Then, the expression levels of each marker were represented by relative values to the expression of GAPDH which was used as a control gene (See FIG. 18).

As shown in FIG. 18, the relative expression of MUSIN 5AC was shown as the highest in the group printed with the bio-ink having the cell content of $1\times10^6$/ml (Group I) among factors related to mucosal tissue differentiation by each group, but in case of KARATIN 14 and BETA-TUBULIN, the group printed with the bio-ink having the cell content of $2\times10^6$/ml (Group II) was the highest. Therefore, it could be seen that it was most suitable to comprise the cell content of $2\times10^6$/ml, when using bio-ink comprising hTMSCs, in preparation of the tracheal replacement support by printing the epithelium part on the porous bellows surface of the present invention.

The invention claimed is:

1. A method of producing an artificial tracheal replacement, comprising
preparing a porous bellows framework having a concave-convex structure using three-dimensional printing technology, comprising
(a) preparing a thermoplastic polymer solution melt by inputting a thermoplastic polymer into a syringe and heating; and (b) dispensing the thermoplastic polymer through a dispensing head nozzle of a three-dimensional printer by applying a physical force,
wherein the dispensing the thermoplastic polymer is performed by printing the thermoplastic polymer solution melt in a dispensing section and a non-dispensing section to produce porous bellows having pores, and wherein the bellows framework is a bellows framework having a surface concave-convex structure which has concave-convex convolutions and grooves in a longitudinal direction on at least one side of outer and inner sides, preparing an annular cartilage part by printing a bio-ink for forming a cartilage part along the circumference of grooves on the outer side of the bellows framework, and preparing an epithelium part by printing a bio-ink for forming an epithelium part on the inner side of the bellows framework.

2. The method of producing according to claim 1, further comprising performing at least a process selected from the group consisting of heating treatment and oxygen plasma treatment, on the produced porous bellows framework.

3. The method of producing according to claim 2, wherein the heating treatment is performed by heating treatment process on the porous bellows framework at 40 to 200° C. for 10 minutes to 60 minutes, and the oxygen plasma treatment process is characterized by treating at 50 to 150 W for 30 minutes to 3 hours.

4. The method of producing according to claim 1, wherein the printing in a dispensing section and a non-dispensing section is controlled by adjusting movement speed of the dispensing head in each section, and the wall thickness and pore formation of the porous bellows framework is controlled by adjusting the distance of the dispensing section and the distance of the non-dispensing section.

5. The method of producing according to claim 1, wherein the dispensing is conducted at an air pressure of 400 to 600 kPa in the dispensing section, or the movement speed of the dispensing head is 60 to 150 nm/min.

6. The method of producing according to claim 1, wherein the length of the non-dispensing section is 300 to 800 μm, and the movement speed of the dispensing head in the non-dispensing section is 200 to 600 mm/min, or the distance between non-dispensing sections is 100 to 1000 μm.

7. The preparation method according to claim 1, wherein the preparation of the cartilage part and preparation of the epithelium part are carried out simultaneously or sequentially.

8. The preparation method according to claim 1, wherein the annular cartilage part and the epithelium part is prepared by printing a bio-ink under the condition of the air pressure of 20 kPa to 200 kPa and the rotation speed of the bellows framework of 3 to 180 DPS (degree per second).

9. The preparation method according to claim 1, wherein the bio-ink comprises a biodegradable hydrogel polymer, and the hydrogel polymer is one or more kinds selected from the group consisting of alginate, gelatin, fibrin, hyaluronic acid, and decellularized tissue derived hydrogel.

10. The preparation method according to claim 9, wherein the bio-ink further comprises one or more kinds selected from the group consisting of a cell, a growth factor, and a non-biodegradable polymer.

11. The preparation method according to claim 1, wherein the preparation method further comprises preparing an absorption prevention part of cartilage part on the outer side of the cartilage part with three-dimensional printing, wherein the absorption prevention part of cartilage part is prepared by dispensing and printing the melt obtained by heating a biodegradable thermoplastic polymer to 60° C. to 200° C., at the air pressure of 400 to 600 kPa, and laminating at least a printing layer with a thickness of 80 to 200 μm.

12. The preparation method according to claim 1, wherein the preparation of the cartilage part and preparation of the epithelium part are carried out sequentially.

* * * * *